(12) United States Patent
Chono et al.

(10) Patent No.: US 9,072,489 B2
(45) Date of Patent: Jul. 7, 2015

(54) MEDICAL IMAGE DIAGNOSTIC APPARATUS AND MEDICAL IMAGE CONTOUR EXTRACTION PROCESSING METHOD

(75) Inventors: Tomoaki Chono, Tokyo (JP); Takahiro Kashiyama, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 184 days.

(21) Appl. No.: 13/513,378

(22) PCT Filed: Jan. 5, 2011

(86) PCT No.: PCT/JP2011/050024
§ 371 (c)(1),
(2), (4) Date: Jul. 19, 2012

(87) PCT Pub. No.: WO2011/083789
PCT Pub. Date: Jul. 14, 2011

(65) Prior Publication Data
US 2012/0281895 A1 Nov. 8, 2012

(30) Foreign Application Priority Data

Jan. 7, 2010 (JP) ................................. 2010-001851
Sep. 29, 2010 (JP) ................................. 2010-218440

(51) Int. Cl.
G06K 9/00 (2006.01)
A61B 8/00 (2006.01)
G06T 7/00 (2006.01)

(52) U.S. Cl.
CPC ............... *A61B 8/461* (2013.01); *G06T 7/0012* (2013.01); *G06T 7/0067* (2013.01); *A61B 8/469* (2013.01)

(58) Field of Classification Search
None
See application file for complete search history.

(56) References Cited

U.S. PATENT DOCUMENTS

| 4,783,829 | A  | * | 11/1988 | Miyakawa et al. | ............ | 382/199 |
| 6,816,607 | B2 | * | 11/2004 | O'Donnell et al. | ............ | 382/131 |
| 8,279,239 | B1 | * | 10/2012 | Jensen et al. | .................... | 345/647 |
| 2002/0003900 | A1 | * | 1/2002 | Kondo | ........................... | 382/199 |

(Continued)

FOREIGN PATENT DOCUMENTS

| JP | A-10-261094 | 9/1998 |
| JP | A-2002-224116 | 8/2002 |

(Continued)

OTHER PUBLICATIONS

T.F. Cootes et al. "Active Shape Models—Their Training and Application", Computer Vision and Image Understanding, vol. 61(1), Jan. 1995, pp. 38-59.*

(Continued)

*Primary Examiner* — Vu Le
*Assistant Examiner* — Samah Beg
(74) *Attorney, Agent, or Firm* — Oliff PLC

(57) ABSTRACT

A medical image diagnostic apparatus of the present invention includes: an image display unit that displays a medical image including a target part of an object; an input unit that inputs feature points of the target part; a contour position estimation unit that estimates a contour position of the target part to generate an initial contour; a contour extraction unit that extracts a contour along the shape of the target part using the feature points and the initial contour; and a control unit that displays a composite image, which is obtained by combining the extracted contour and the medical image, on the image display unit.

15 Claims, 19 Drawing Sheets

(56) References Cited

U.S. PATENT DOCUMENTS

| | | | |
|---|---|---|---|
| 2002/0102023 A1 | 8/2002 | Yamauchi | |
| 2003/0097219 A1* | 5/2003 | O'Donnell et al. | 702/19 |
| 2004/0109595 A1* | 6/2004 | Luo et al. | 382/132 |
| 2005/0152592 A1* | 7/2005 | Kasai | 382/132 |
| 2005/0238216 A1 | 10/2005 | Yoden | |
| 2006/0056698 A1* | 3/2006 | Jolly et al. | 382/190 |
| 2006/0072802 A1* | 4/2006 | Higgs et al. | 382/131 |
| 2007/0014454 A1* | 1/2007 | Sawyer et al. | 382/128 |
| 2008/0075375 A1* | 3/2008 | Unal et al. | 382/243 |
| 2009/0123047 A1* | 5/2009 | Yfantis | 382/131 |
| 2009/0268956 A1* | 10/2009 | Wiley | 382/131 |
| 2009/0297012 A1* | 12/2009 | Brett et al. | 382/132 |
| 2010/0177946 A1* | 7/2010 | De Bruijne et al. | 382/132 |
| 2012/0327075 A1* | 12/2012 | Zagorchev et al. | 345/419 |
| 2013/0066189 A1* | 3/2013 | Zagorchev et al. | 600/407 |
| 2013/0236108 A1* | 9/2013 | Matsuda et al. | 382/203 |

FOREIGN PATENT DOCUMENTS

| | | |
|---|---|---|
| JP | A-2004-121834 | 4/2004 |
| JP | A-2005-218796 | 8/2005 |
| JP | A-2007-014542 | 1/2007 |
| JP | A-2007-265331 | 10/2007 |
| JP | A-2009-153600 | 7/2009 |
| JP | A-2009-172186 | 8/2009 |

OTHER PUBLICATIONS

T.F. Cootes et al. "The Use of Active Shape Models for Locating Structures in Medical Images", Image and Vision Computing, vol. 12(6), Jul. 1994, pp. 355-366.*

Nishiura et al. "Active Contour Extraction Method Using Partial Shape Constraint Contour Model", Systems and Computers in Japan, vol. 31(14), Jan. 2000, pp. 183-190.*

International Search Report issued in International Application No. PCT/JP2011/050024 dated Feb. 1, 2011.

Dec. 27, 2013 Office Action issued in Chinese Patent Application No. 201180005558.3.

* cited by examiner

FIG.14
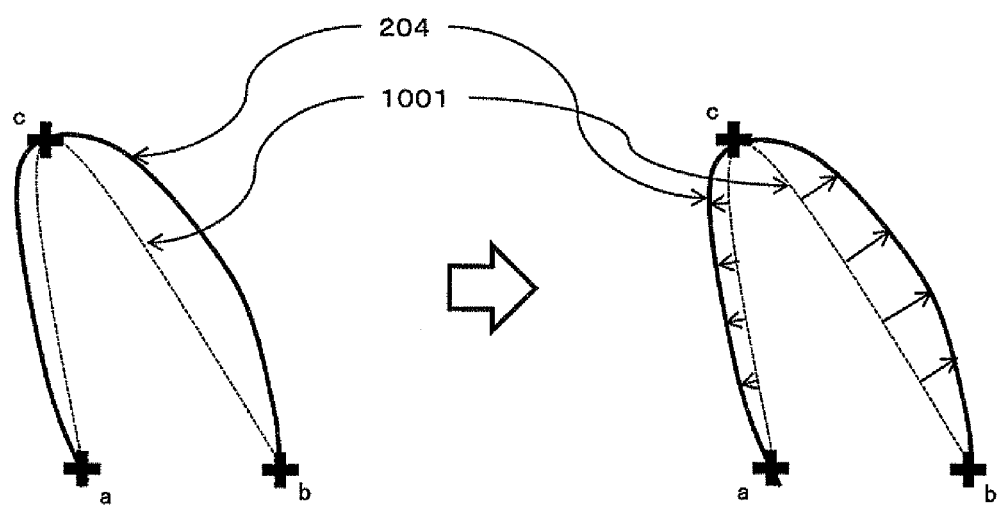
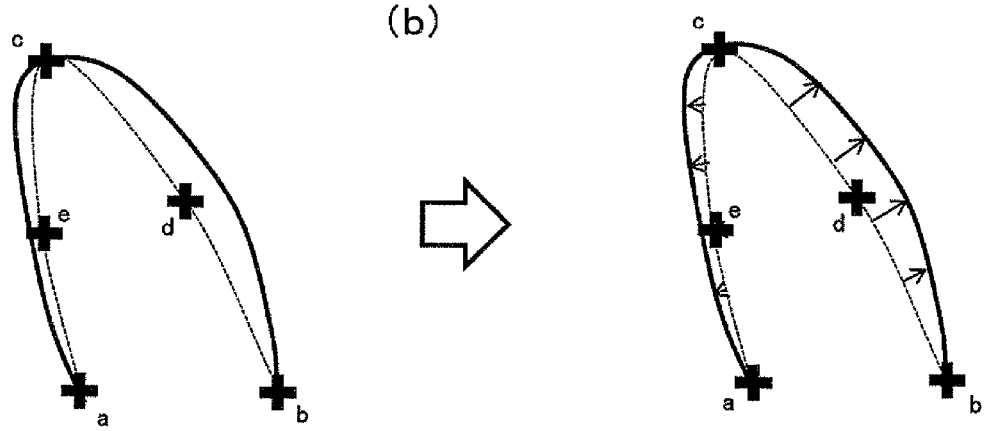

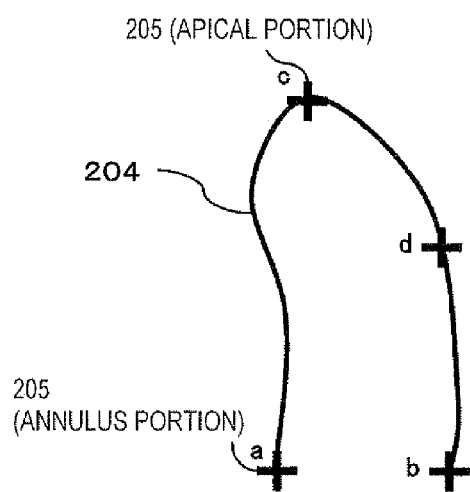 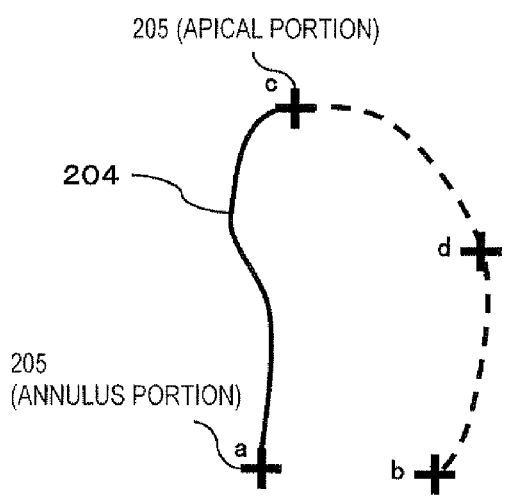
FIG.16

MEDICAL IMAGE DIAGNOSTIC APPARATUS AND MEDICAL IMAGE CONTOUR EXTRACTION PROCESSING METHOD

TECHNICAL FIELD

The present invention relates to a medical image diagnostic apparatus and a method for processing of extracting a target contour of a medical image, which are for improving the accuracy in processing of extracting a contour of a target part of a medical image of an object.

BACKGROUND ART

Shape information of a target part of an object is one of the important information to diagnose the stage of progression of the lesion. Here, the shape information of the target part indicates the shape and the size of the target part.

In medical image diagnostic apparatuses, such as an ultrasonic diagnostic apparatus, an X-ray image diagnostic apparatus, an X-ray CT apparatus, and a magnetic resonance imaging apparatus, the shape information of the target part of the object can be measured non-invasively. The shape information of the measured target part is displayed as a medical image on a display device.

Moreover, in the medical image diagnostic apparatuses, there is a demand from an examiner that the examiner wants to measure the shape information of the target part of the object more accurately.

Therefore, PTL 1 and PTL 2 have been proposed as one image processing method to meet the demand. The image processing method disclosed in PTL 1 is performed in each of the following steps.

In the first step, an initial contour generation unit generates contour points of a plurality of initial contours of a target part.

In the second step, the examiner designates candidate points of the contours of the target part in the image.

In the third step, an initial contour selection unit selects actual contour points from the contour points of the plurality of initial contours at the positions closer to the target part.

In the fourth step, the initial contour selection unit extracts the contour of a target in the image by changing the shape of the selected initial contour such that the sum of internal energy showing the contour shape, image energy showing the characteristics of the image, and external energy given when necessary are minimized.

Moreover, in the image processing method disclosed in PTL 2, standard shape data of the boundary of the myocardium/heart chamber in the atrium or the ventricle, which has the image data collection conditions (for example, an ultrasonic scanning method, a scanning direction, or a scanned cross section for the organ to be diagnosed (heart)) as a parameter, is stored in advance, and preferable standard shape data is read on the basis of the image data collection conditions added to the image data and also the contour data is generated on the basis of the positional information of the amount of features (two points of an annulus portion and one point of apical portion) of the myocardium set by an input unit.

CITATION LIST

Patent Literature

[PTL 1] JP-A-10-261094
[PTL 2] JP-A-2007-14542

SUMMARY OF INVENTION

Technical Problem

In the image processing method disclosed in PTL 1, however, an operation of extracting actual contour points is within the range of contour points of a plurality of initial contours. For this reason, there has been an unsolved problem in that the accuracy of the operation of extracting the actual contour points is not sufficient when the actual contour point deviates from the contour points of the plurality of initial contours due to pulsation of moving organs, such as the heart.

In addition, when measuring the sizes of a plurality of cava as in the heart or when measuring the size of a region interposed between the intima surface and the adventitia surface of tissue, a plurality of contours are required. In both the image processing methods disclosed in PTL 1 and PTL 2, however, it is necessary to input a plurality of candidate points or the positional information of the amount of features for each extracted contour. Accordingly, the operation burden of the examiner is large.

Therefore, it is an object of the present invention to provide a medical image diagnostic apparatus and a medical image contour extraction processing method capable of measuring the information regarding the shape of a target part of an object more accurately so that the operation burden of the examiner can be reduced.

Solution to Problem

In order to achieve the above-described object, the present invention estimates a contour position of a target part of an object to generate an initial contour, extracts a contour along the shape of the target part using the input feature points of the target part and the initial contour, and displays a composite image obtained by combining the extracted contour and a medical image on the image display unit.

Specifically, a medical image diagnostic apparatus of the present invention includes: an image display unit that displays a medical image including a target part of an object; an input unit that inputs feature points of the target part; a contour position estimation unit that estimates a contour position of the target part to generate an initial contour; a contour extraction unit that extracts a contour along a shape of the target part using the feature points and the initial contour; and a control unit that displays a composite image, which is obtained by combining the extracted contour and the medical image, on the image display unit.

In addition, a medical image contour extraction processing method of the present invention comprising: a step of displaying a medical image including a target part of an object by means of an image display unit; a step of inputting feature points of the target part by means of an input unit; a step of estimating a contour position of the target part to generate an initial contour by means of a contour position estimation unit; a step of extracting a contour along a shape of the target part using the feature points and the initial contour by means of a contour extraction unit; and a step of displaying a composite image, which is obtained by combining the extracted contour and the medical image, on the image display unit by means of a control unit.

Advantageous Effects of Invention

According to the present invention, since the information regarding the shape of a target part of an object can be measured more accurately, there is an effect that a medical image diagnostic apparatus and a medical image contour extraction processing method capable of reducing the operation burden of the examiner are provided.

BRIEF DESCRIPTION OF DRAWINGS

FIG. 14 is a view showing the contour extraction using a curve model of a fourth embodiment.

FIG. 16 is a view showing an example of a sixth embodiment where the number of feature points is not 3 but 4.

DESCRIPTION OF EMBODIMENTS

Embodiments will be shown below.

First Embodiment

A first embodiment of the present invention will be described using the drawings.

The first embodiment is a method of extracting the contour of the boundary of the myocardium which moves with time due to beating of the heart.

Figure 1:
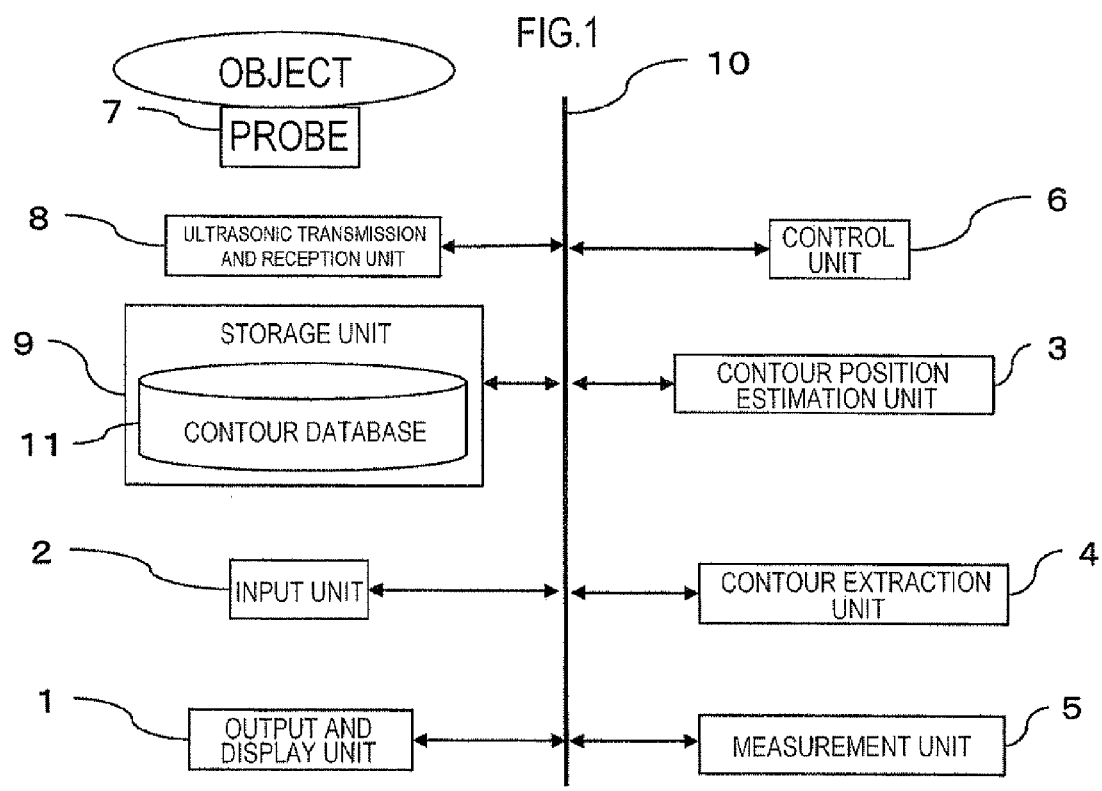
FIG. 1 is a block diagram showing an example of the schematic configuration of an ultrasonic diagnostic apparatus of the present invention.

FIG. 1 is a block diagram showing an example of the schematic configuration of a medical image diagnostic apparatus of the present invention.

The medical image diagnostic apparatus related to the present invention includes an output and display unit 1, an input unit 2, a contour position estimation unit 3, a contour extraction unit 4, a measurement unit 5, a control unit 6, and a storage unit 9.

The output and display unit 1 displays and outputs a medical image including a target part of an object or the related information of the medical image. Specific display and output targets in the output and display unit 1 are not only a medical image but also contour lines and measured values or the measurement report of the measured values. Display and output targets are output to a video printer, output as a film, or output as an electronic file to a personal computer connected through a network.

The input unit 2 is an interface for performing various operations of the diagnostic apparatus. Specifically, among the various operations, the input unit 2 sets the position of a target part displayed on the output and display unit 1. In addition, the input unit 2 is an input device, such as a keyboard, a track ball, a switch, and a dial, and is used to designate the type or feature points of body tissue.

The contour position estimation unit 3 generates an initial contour by estimating the contour position of a target part by setting the position, size, and angle of the heart on the basis of the type or feature points of the heart set using the input unit 2. A method based on the active contour model is used for the generation of the initial contour. For example, the active contour model is expressed by a set of apexes which make up the contour line of the myocardium of the heart present on a medical image. The set of apexes which make up the contour line repeats meandering like a snake to form a contour line changing from moment to moment.

Moreover, it is also possible to use a curve model which uses a curve function, such as a spline curve, in addition to the active contour model for the generation of the initial contour.

In addition, the contour position estimation unit 3 estimates the number of contours or the position of the contour on the basis of the measurement item set by the input unit 2 or the position of body tissue. In this case, the accuracy of the position, size, shape, or the like of the estimated contour does not matter. As an example in the embodiment, a mathematical calculation method of a contour which matches the set measurement item or the position of body tissue may be stored in advance in the storage unit 9 as a program, and the contour position estimation unit 3 may read this program to set a contour. As an example of the mathematical calculation method of a contour, a method may be considered in which the contour of the left ventricle is expressed by the mathematical function and is disposed on the basis of the position, angle, and size calculated from the set position, for example.

As another method, it may be set by extracting from a contour database 10 the information regarding the number of contours or the position of a contour corresponding to the measurement item or the set position.

The contour extraction unit 4 performs an operation to extract a contour using the initial contour calculated by the contour position estimation unit 3. Known Active Contour Model (abbreviated as "ACM"), Active Shape Model (abbreviated as "ASM"), and Active Appearance Model (abbreviated as "AAM") are used as methods for the operation. The contour extraction operation also includes smoothing processing for smoothly connecting a group of contour points extracted at the same time.

The contour extraction unit 4 performs processing for changing the shape of the initial contour so as to fit the contour of body tissue using the contour extraction method which uses edge detection or the like, for example. In this case, the contour extraction unit 4 may be operated to extract the contour at the more accurate position while referring to the contour database 11. For example, a contour extraction method based on a model, such as the active contour model, may be applied. The shape of the extracted contour may be changed to a smooth shape using a curve model, such as the spline curve, and this result is displayed on the screen of the apparatus together with the image by the output and display unit 1.

The measurement unit 5 calculates measurement items regarding the shape of the contour (measured values regarding the shape of the extracted contour), such as the length, area, and volume regarding the extracted contour. For example, the measurement items are coordinates of the contour point or center position coordinates of a region surrounded by the contour line, the boundary length of the contour line, and the area and volume surrounded by the contour line. The volume is calculated by a calculation method called the Simpson method. The Simpson method is a calculation method which divides a volume calculation region of the ventricle into a plurality of stacked cylindrical disks and calculates the volume of the ventricle by the sum of the volumes of the respective disks when calculating the volume of the ventricle using a medical image, for example. Details of this method are disclosed in JP-T-2007-507248.

In addition, the volume calculation method which is not based on the Simpson method is performed by the following procedure.

First, the input unit 2 sets a target region whose volume is to be measured in a medical image displayed on the output and display unit 1. Then, the control unit 6 performs an operation to divide the target region into a plurality of volume elements. Then, the control unit 6 calculates the amount of movement of the apex of the volume elements caused by movement of the target region. Then, the control unit 6 calculates the volumes of the volume elements after the movement using the amount of movement of the apex. Finally, the control unit 6 calculates the volume of the target region by calculating the sum of the volumes of the volume elements after the movement.

In addition to this, for example, in the case of an ultrasonic image of the heart, a known measurement method such as the Area-length method or the Modified Simpson method may be applied for the volume. The measured value is displayed on the display of the apparatus together with an ultrasonic image by the output and display unit 1.

Moreover, in addition to performing the operation described above, the control unit 6 controls each component of the entire medical image diagnostic apparatus and also controls the output and display unit 1, the contour position estimation unit 3, the contour extraction unit 4, and the measurement unit 5 when the type or feature points of body tissue have been changed. For example, a central processing unit is used as the control unit 6.

In addition, the contour position estimation unit 3, the contour extraction unit 4, and the measurement unit 5 are functions realized when the control unit 6, which is a central processing unit, reads each program stored in the storage unit 9 and executes it.

Programs for operating various systems which form the medical image diagnostic apparatus are stored in the storage unit 9. In addition, image data and contour model data (data as a reference for generating an initial contour) for each type of body tissue related to a target part are stored in the storage unit 9. For example, the storage unit 9 is a storage medium, such as a semiconductor memory, a hard disk, and an optical disc. In addition, the storage unit 9 may be an external storage medium through a network.

In addition, the storage unit 9 includes the contour database 11. The information regarding the number of contours or the position or the shape of a contour corresponding to the measurement item or the measurement position is stored in the contour database 11. Such information is used for contour extraction of the contour position estimation unit 3 and the contour extraction unit 4.

A system bus 10 is a data transfer bus for performing data communication with connected hardware. The output and display unit 1, the input unit 2, the contour position estimation unit 3, the Contour extraction unit 4, the measurement unit 5, the control unit 6, and the storage unit 9 are connected to the system bus 10.

In addition, an ultrasonic diagnostic apparatus will be described as an example of the medical image diagnostic apparatus of the present invention. The ultrasonic diagnostic apparatus further includes a probe 7 and an ultrasonic transmission and reception unit 8.

The probe 7 is brought into contact with the body surface of the target part of the object to transmit an ultrasonic signal to the target part and also receive a reflected echo signal from the target part. The probe 7 is formed by transducer elements of a plurality of channels. When it is classified according to the material of the transducer element, there are a piezoelectric element, a capacitive micromachined. Ultrasonic Transducer (cMUT), and the like. A probe of any dimension may be adopted. In addition, it is possible to use any type of probe 7, such as a linear type, a convex type, and a sector type.

The ultrasonic transmission and reception unit 8 generates an image of body tissue of the object, and has a signal transmission function and a signal reception function. The signal transmission function is to transmit an ultrasonic signal from the probe 7 to the object. The signal reception function is to receive a reflected echo signal of the ultrasonic signal transmitted from the probe 7 to the object, perform signal processing through a phasing circuit or an amplifier circuit according to an imaging setting of the apparatus, and acquire a phased ultrasonic signal. In addition, the ultrasonic transmission and reception unit 8 generates an ultrasonic image on the basis of the imaging setting of the apparatus from the ultrasonic signal, for example, a scanning range of an ultrasonic bean, gain setting, or the like. This ultrasonic image is always updated according to the frame rate determined by the imaging setting. That is, the ultrasonic image is displayed as an image on the display of the ultrasonic diagnostic apparatus by the output and display unit 1.

Hereinafter, the first embodiment will be described for the case where an ultrasonic diagnostic apparatus is used.

Next, an operation of the first embodiment will be described using FIG. 2.

Figure 2:
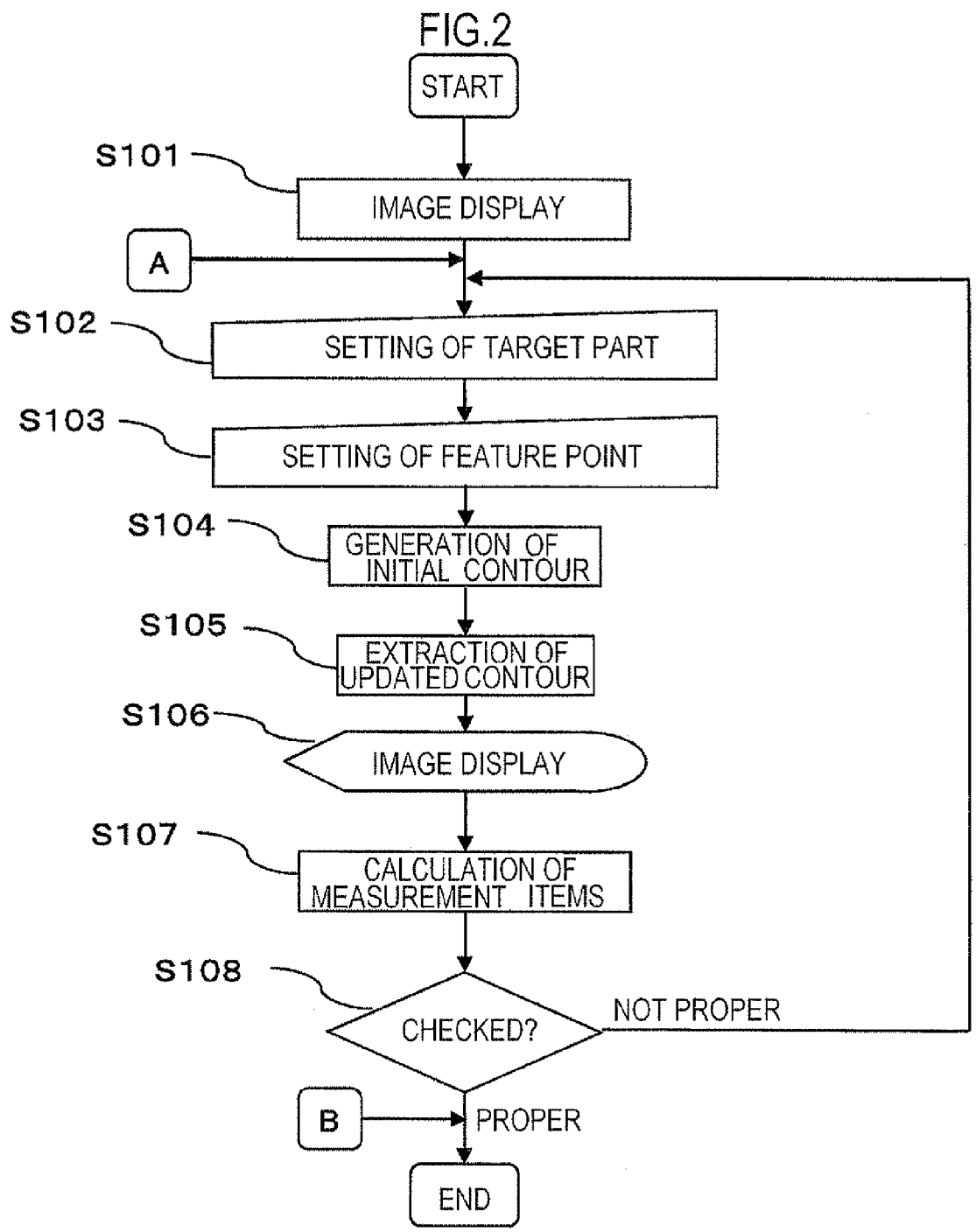
FIG. 2 is a flow chart showing the operation procedure of a first embodiment.

FIG. 2 is a flow chart showing the operation procedure of the first embodiment.

The examiner sets an ultrasonic image of the heart used for diagnosis by the operation of the input unit 2 so that the ultrasonic image can be displayed on the output and display unit 1. The control unit 6 receives the operation information of the input unit 2 and displays an ultrasonic image, in which the heart as a target part is extracted, on the display screen of the output and display unit 1 (S101).

The examiner sets the feature points of the target part (type of body tissue) and the heart by the operation of the input unit 2 (S102 and S103).

Figure 3:
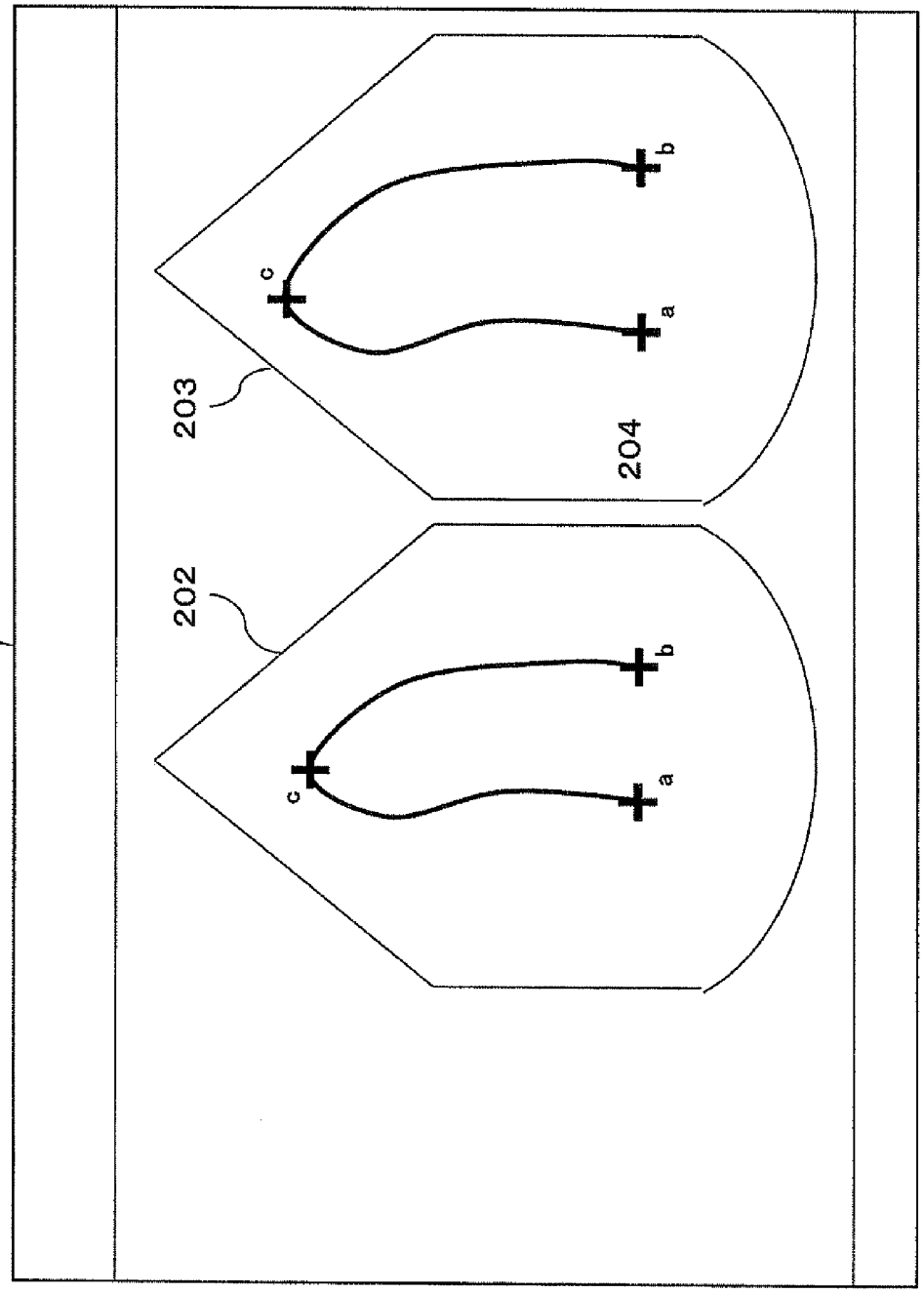
FIG. 3 is a view showing an example of the operation screen of an examiner using an image of an output and display unit 1.

FIG. 3 is a view showing an example of the operation screen of an examiner using an ultrasonic image of the output and display unit 1.

As shown in FIG. 3, the examiner sets a cross-sectional image of an ultrasonic image of the heart by the operation of the input unit 2 while viewing the image on the display screen of the output and display unit 1. As examples of the cross-sectional image of the ultrasonic image of the heart, an end diastole image and an end systole image of each of an Apical Two Chamber (A2C) image 202 and an Apical Four Chamber (A4C) image 203 are set.

First, the examiner inputs feature points of the ultrasonic image of the heart of the output and display unit 1 using the input unit 2.

For example, the examiner operates a track ball to drag the caliber indicating the feature point, and inputs three feature points of a point at the septal side of an annulus portion as a start point a, a point at the side wall side as an end point b, and an apical point c of an apical portion.

Then, the control unit 6 makes the contour position estimation unit 3 generate an initial contour (S104).

For example, the contour position estimation unit 3 generates the initial contour by estimating the contour position of the target part by specifying one item of the contour model data, which is stored in advance in the storage unit 9, on the basis of the type of body tissue set in S102 and adjusting the center position, size, and inclination of the specified contour model data according to the positions of the feature points a, b, and c of the heart on the image set in S103. In addition, the initial contour may be a set of points or may be a function showing the curve.

Figure 4:
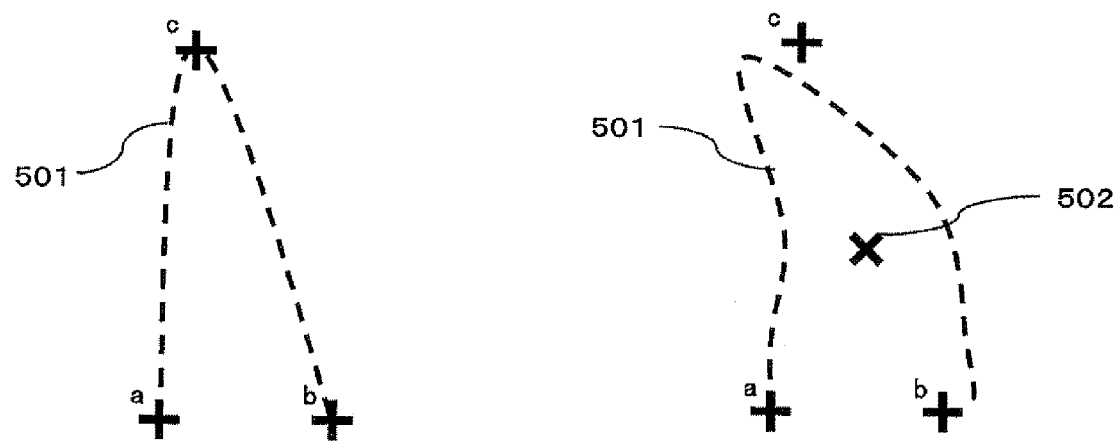
FIG. 4 is a view illustrating the principle of generating an initial contour from three feature points.

FIG. 4 is a view illustrating the principle of generating an initial contour from three feature points.

FIG. 4(a) is an example where the curve passing through the three feature points is set as an initial contour 501. Here, the feature points are two points of annuli a and b and one point of the apex cordis c. A function, such as a polynomial curve, a spline curve, or an elliptic curve, is used as the curve. The initial contour may be used as an initial contour based on the active contour model (ACM) or an initial position of boundary detection. In this case, the equation of a function which defines a curve is the contour model data, and defining a coefficient of the equation on the basis of feature points is equivalent to adjusting the center position, size, and inclination of the contour model data.

In addition, a contour model based on another method is when an initial contour does not pass through feature points, as shown in FIG. 4(b). When the initial contour does not pass through the feature points (in the active shape model (ASM) or the active appearance model (AAM)), the center position of a contour, the size of a contour, and the inclination of a contour are generally given to the contour model data to generate the initial contour 501. Processing of generating the initial contour will be specifically described. First, the contour position estimation unit 3 calculates the coordinates of a center position 502 of a contour from the coordinates of the three feature points as coordinates of the center of gravity. Then, the contour position estimation unit 3 calculates the size of the contour on the basis of a distance from the coordinates of the center to each of the three feature points. Finally, the contour position estimation unit 3 calculates the inclination of the contour from the angle of the coordinates with respect to the center.

Figure 5:
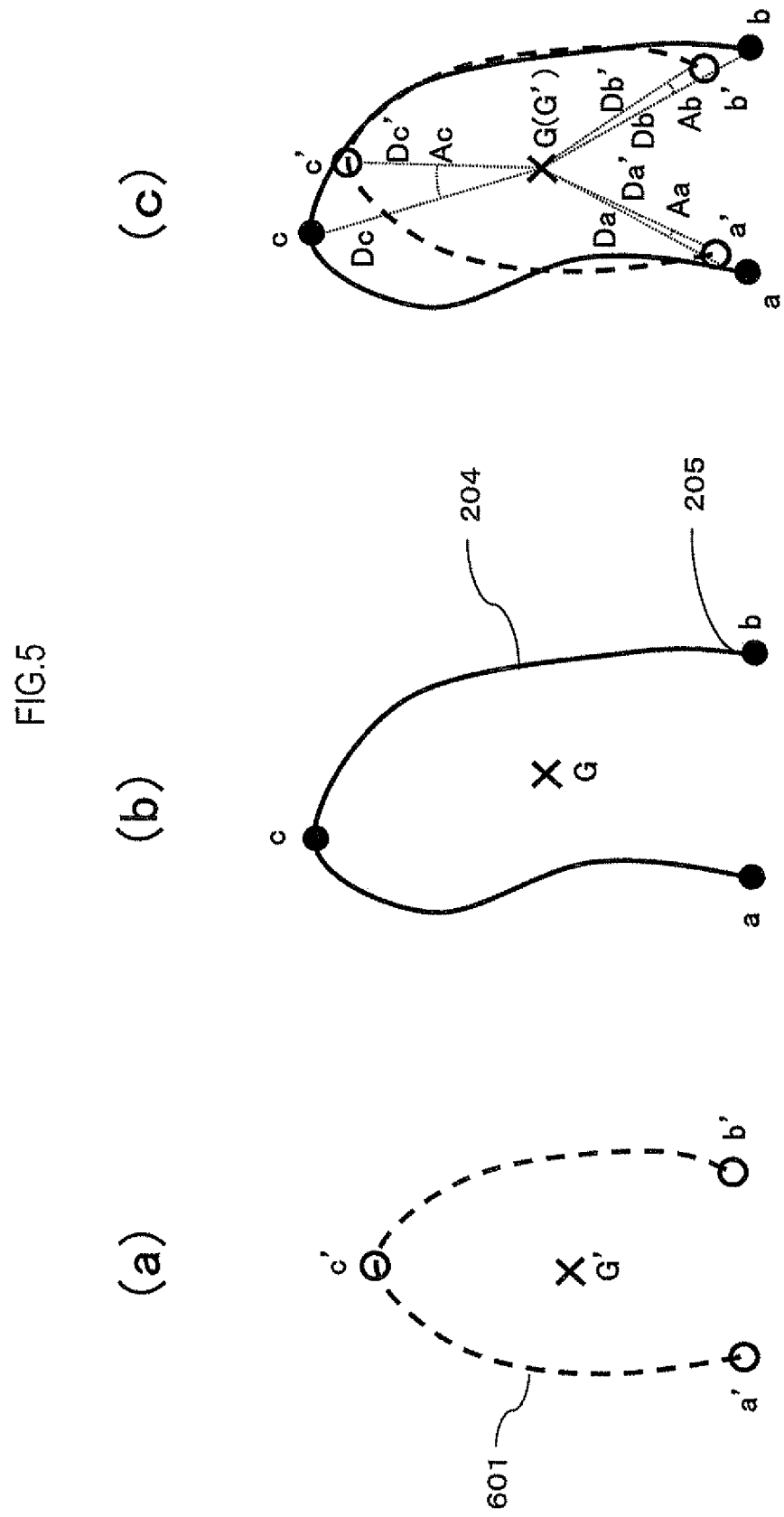
FIG. 5 is a view showing the principle of a specific method of calculating the center position, size, and inclination of a contour.

FIG. 5 is a view showing the principle of a specific method of calculating the center position, size, and inclination of a contour. FIG. 5(a) shows contour model data 601. White circles in the drawing are feature points, and indicate two points of the annulus and one point of an apical portion. Data obtained by averaging a plurality of contour point coordinates acquired in the past may be used as the contour model data in the active shape model (ASM) or the active appearance model (AAM), for example. FIG. 5(b) is a left ventricle contour 204 which is to be actually extracted. In addition, black circles in the drawing are feature points 205 set in S103. Using the contour model data 601 and the coordinate information of the feature points of the white circles and the black circles, the shape of the contour model data 601 is adjusted so that the contour model data 601 is brought as close to the left ventricle contour 204 as possible.

The shape information of the contour model data 601 and the left ventricle contour 204 is calculated from the coordinates of the white circles and the black circles shown in FIG. 5(c).

FIG. 5(c) is a view illustrating a specific method of calculating the shape information of the contour model data 601 and the left ventricle contour 204. First, adjustment of the center positions of the contour model data 601 and the left ventricle contour 204 will be described. The center of gravity of the three feature points a', b', and c' is calculated as the center position G' of the contour model data 601. Then, the center of gravity of the three feature points a, b, and c is calculated as the center position G of the left ventricle contour 204. The centre position G' of the contour model data 601 in FIG. 5(a) is adjusted so as to match the center position G of the left ventricle contour 204 in FIG. 5(b).

Next, adjustment of the size of a contour will be described. The adjustment of the size is made according to the distance from the center position G to each of the three points a, b, and c. In the case of the contour model data 601, distances Da', and Db' from the center position G' to the respective feature points a', b', and c' are calculated. In the case of the left ventricle contour 204, distances Da, Db, and Dc from the center G to the respective feature points a, b, and c are calculated. Then, the ratios of the distance between the contour model data 601 and the left ventricle contour 204 at the feature points are Da/Da', Db/Db', and Dc/Dc' Then, the average ratio Dave of the ratios of Da/Da', Db/Db', and Dc/Dc' is calculated. Finally, when Da is taken as an example for explanation, expansion or reduction to the size of the average contour of the left ventricle can be performed by multiplying Da' by Dave around the center. In addition, similarly for Db' and Dc', expansion or reduction to the size of the average contour of the left ventricle can be performed by multiplying Db' and Dc' by Dave around the center.

Next, adjustment of the inclination of a contour will be described. For the adjustment of an inclination, an angle Aa between the line segment G'a', which connects the center position G' and the feature point a' of the contour model data 601 to each other, and the line segment Ga, which connects the center G and the feature point a of the left ventricle contour 204 to each other, is calculated.

Similarly for the feature points b and c, an angle Ab between the line segment G'b' connecting the center position G' and the feature point b' of the contour model data 601 to each other and the line segment Gb connecting the center G and the feature point b of the left ventricle contour 204 to each other is calculated, and an angle Ac between the line segment G' c' connecting the center position G' and the feature point c' of the left ventricle contour to each other and the line segment Gc connecting the center G and the feature point c of the left ventricle contour to each other is calculated.

In addition, the average angle Aave of the angles Aa, Ab, and Ac is calculated. Therefore, the initial contour can be generated by rotating the contour model data 601 around G' to return it by the average angle Aave so that the contour model data 601 approximately matches the inclination of the left ventricle contour.

In the above processing, it becomes possible to generate the initial contour 501 close to the shape of the left ventricle contour 204 by setting the center position G of the contour model data 601, and the average ratio Dave, and the average angle Aave.

The control unit 6 makes the contour extraction unit 4 extract a contour (S105). A contour is extracted from the initial contour in S104 using a contour model which changes its shape actively. The extracted contour is screen-displayed as the extracted contour 204 in FIG. 2.

Figure 6:
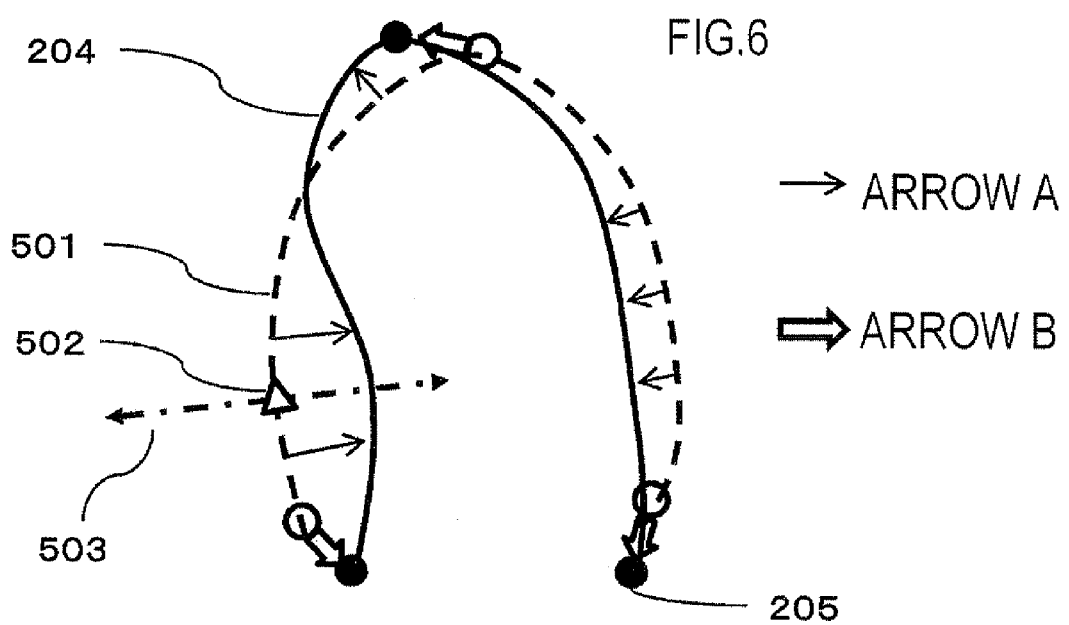
FIG. 6 is a view illustrating a specific operation example of a contour extraction unit 4.

FIG. 6 is a view illustrating a specific operation example of the contour extraction unit 4. The contour extraction process is a process of approximating the initial contour 501 shown in FIG. 6 to the left ventricle contour 204. Examples of the method for the approximation process are contour models which change their shapes actively, such as the active contour model (ACM), the active shape model (ASM), and the active appearance model (AAM). The contour line calculated by the contour model is formed by a plurality of contour points, and the positions of the contour points move according to a change in the shape of the contour line.

In the contour model which changes its shape actively, generally, all contour points are controlled in a direction moving closer to the wall surface of the myocardium (direction of arrow A). For example, boundary detection processing is performed toward a direction perpendicular to the contour line, so that the contour points are moved toward a direction in which the boundary of the wall surface of the myocardium is present (toward a direction of arrow A). In the example of FIG. 6, contour points are moved toward the left ventricle contour 204 in a vertical direction from the initial contour 501.

Specifically, the contour extraction unit 4 performs boundary detection processing for a predetermined range 503 in a direction, which crosses the contour point 502 and is perpendicular to the initial contour 501, for each contour point 502 on the initial contour 501. Tens of contour points 502 are set on the initial contour 501. In addition, the predetermined range 503 is assumed to include about tens of pixels in order to increase the speed of processing and to make a contour smooth. Known methods can be applied for the boundary detection processing. For example, the contour extraction unit 4 specifies observed pixels one by one from the pixel group, which is included in the predetermined range 503, in a direction perpendicular to the initial contour 501 and calculates the amount of changes in the observed pixels. For example, the amount of change in the observed pixel is the sum of difference values between the pixel value of the observed pixel and the pixel values of adjacent pixels (two adjacent left and right points or four adjacent left, right, upper, and lower points, or the like). In addition, the contour extraction unit 4 detects a pixel with the largest amount of change, among pixels in the predetermined range 503, as a position of the "boundary" (in the present embodiment, the left ventricle contour 204). In addition, the contour extraction unit 4 moves the contour point 502 to the position detected as the "'boundary".

However, as an exception, the contour extraction unit 4 moves the feature points (white circles) on the initial contour in the direction of arrow B approximating to the feature points (black circles) 205 of the left ventricle contour.

The feature points 205 are designated by the examiner in order to indicate some positions of a contour, and are reference points of a contour called the start point a, end point b, and apical point c of the contour. The contour extraction unit 4 extracts a contour so as to pass through the start point a, the end point b, and the apical point c which are reference points (feature point 205) of the contour.

That is, the contour extraction unit 4 extracts a contour so as to pass through the feature point 205 and the contour point 502 after being moved to the position detected as the "boundary".

Finally, the contour line has a shape along the wall surface of the myocardium which passes through the three feature points. Therefore, even if the initial contour 501 does not pass through the feature point 205 of the left ventricle contour, a contour passing through the designated feature point 205 on the left ventricle contour is extracted when the contour extraction processing is completed.

In order to connect the contour points smoothly, the control unit 6 extracts a final contour line using a smoothing curve, such as the spline curve. In addition, the control unit 6 makes the measurement unit 5 calculate measurement items, such as the length, area, and volume of a target part, on the basis of the extracted contour line (S106). In the example of the left ventricle, a Modified Simpson method or an Area Length method is used as a volume measurement method. After calculating the volumes in both an end diastole image and an end systole image, the cardiac ejection fraction can be calculated as a value obtained by dividing the difference between the end diastole volume and the end systole volume by the end diastole volume.

The control unit 6 displays the measurement items calculated by the measurement unit 5 together with the image shown on the output and display unit 1 in FIG. 3 (S107).

Figure 7:
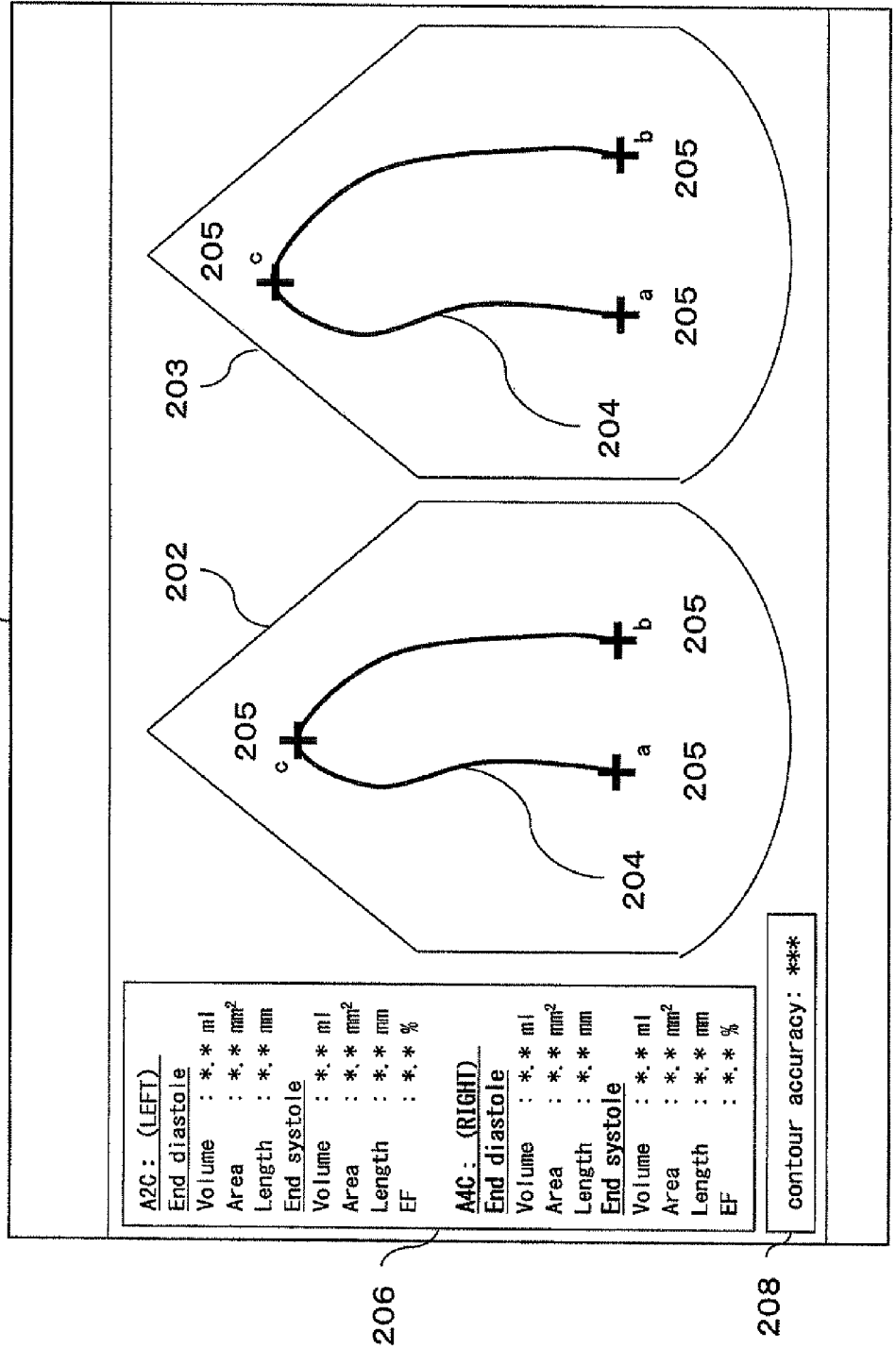
FIG. 7 is a view showing an example where an image and measurement items are displayed on the output and display unit 1.

FIG. 7 is a view showing an example of displaying an image and measurement items on the output and display unit 1.

FIG. 7 shows an example of displaying the ultrasonic images 202 and 203, the extracted contour 204, and a measured value 206 side by side.

The examiner checks whether or not the contour has been extracted properly (S108). The contour extracted by processing until the previous step S107 is checked on the screen. If there is no need to change the contour, the process ends. If the contour needs to be changed, the process is performed again from the setting of the type of body tissue and feature points in S102 and S103. The examiner performs fine adjustment of the contour line manually using the input unit 2 when necessary. Specifically, the examiner changes the position of the contour manually by dragging and dropping the contour line with a mouse, for example.

As described above, in the first embodiment, the output and display unit 1 displays a medical image including a target part of an object, the input unit 2 sets the type of body tissue and feature points related to the target part while referring to the display of the medical image, the contour position estimation unit 3 generates an initial contour on the basis of the position of the target part, the contour extraction unit 4 extracts a contour along the shape of the target part using the initial contour and the feature points, and the control unit 6 displays a composite image obtained by combining the extracted contour and the medical image on the output and display unit 1. Therefore, since a contour along the shape of the target part using the initial contour and the feature points is extracted, a contour along the shape of a moving organ can be extracted every contour extraction operation when the target part is a moving organ with large individual difference of an object. As a result, the accuracy in extracting the target part of the object can be improved.

In addition, since the examiner can check the measurement items (for example, length, area, and volume) of the target part in real time while observing the composite image displayed on the image display unit in order to check whether or not the contour matches the shape of the target part, the shape information of the target part of the object can be measured more accurately.

In addition, a unique effect of the first embodiment is that the 2AC image 202 and the 4AC image 203 of the heart can be comprehensively evaluated since two or more different images, such as the 2AC image 202 and the 4AC image 203 of the heart, are displayed and measurement items of a target part of each of the images are calculated.

Second Embodiment

In a second embodiment of the present invention, an example will be described in which a contour, which changes with movement of a moving organ such as beating of the heart, is extracted following the temporal change.

In the second embodiment, the configuration of hardware of an ultrasonic diagnostic apparatus and S101 to S108 of software to execute are the same as those in the first embodiment. Accordingly, only the differences will be described.

Figure 8:
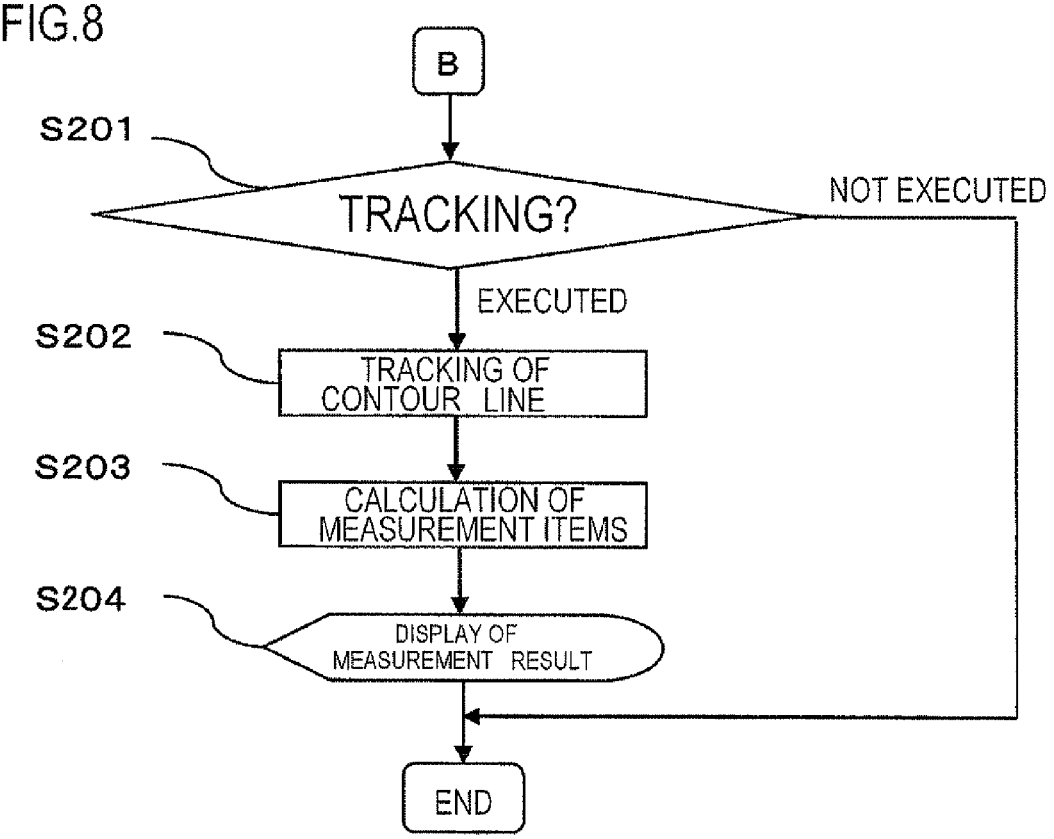
FIG. 8 is a flow chart showing the operation procedure of a second embodiment.

FIG. 8 is a flow chart showing the operation procedure of the second embodiment.

Since the second embodiment is performed subsequent to the determination of "appropriateness" in S108 of the first embodiment, the flowchart in FIG. 8 is connected to a terminal B of the flow chart in FIG. 2.

The examiner sets execution/no execution of a tracking operation, in which region extraction is performed so as to follow beating of the heart in an ultrasonic image, by the operation of the input unit 2. The control unit 6 determines whether to set the tracking operation to "execution" or "no execution" according to the operation of the input unit 2. If the determination result is "execution", the process proceeds to S202. If the determination result is "no execution", the process ends (S201).

The control unit 6 detects the movement positions of feature points of contour points for each frame using a tracking method (S202). The tracking method is disclosed in JP-A-2004-121834, for example. The contour line is uniquely determined if the feature points are determined. Accordingly, it is not necessary to perform tracking for all contour points, and it is preferable to detect only movements of the feature points by tracking. The control unit 6 generates a contour line using the feature points tracked in each frame.

The control unit 6 makes the measurement unit 5 calculate a measurement item in each frame (S203). The calculation of a measurement item is the same as S105, but is different in that time-series data is obtained in S203 while a measured value of a single phase is calculated in S105.

The control unit 6 displays the measured value on the output and display unit 6 (S204).

Figure 9:
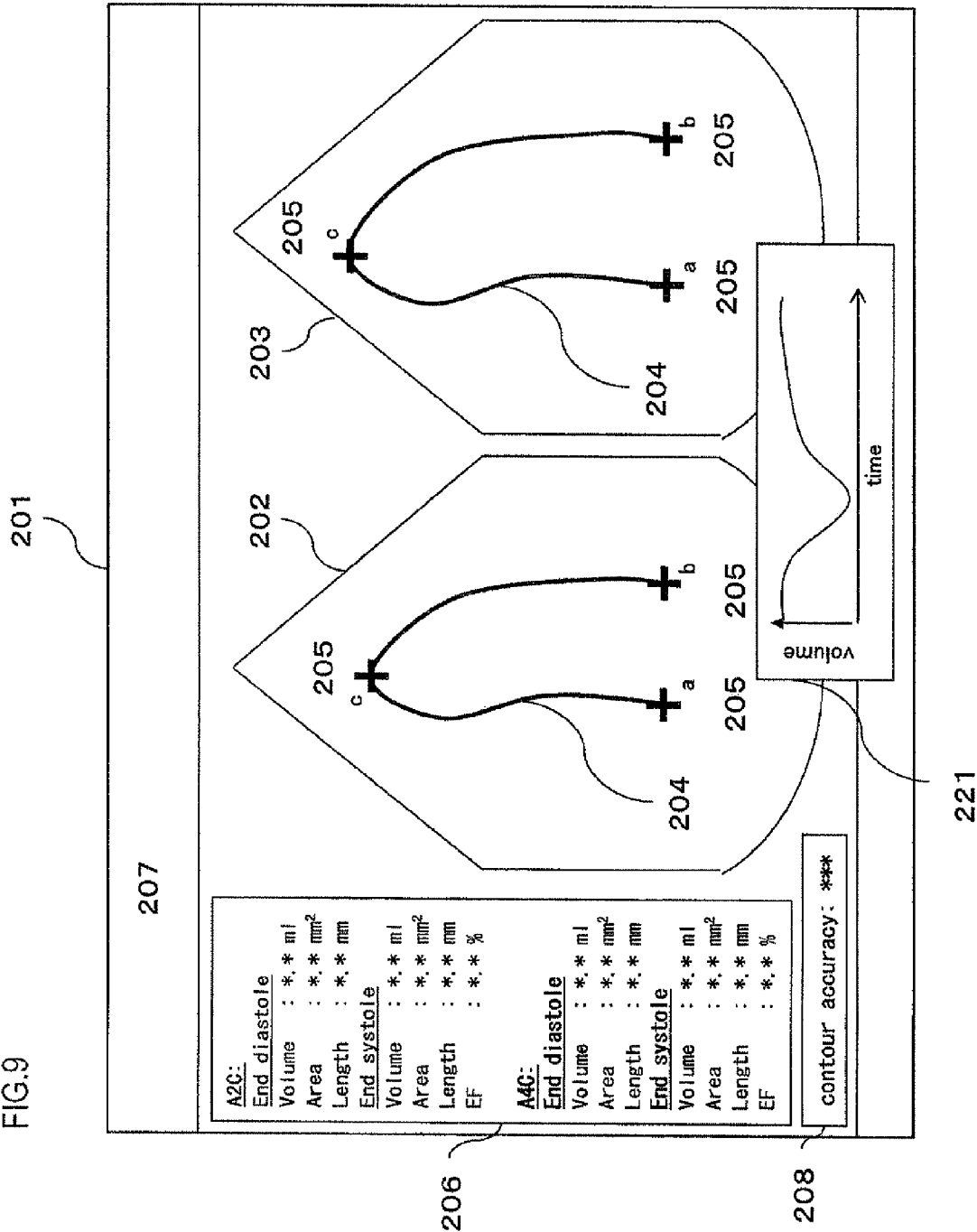
FIG. 9 is a display screen for measuring a temporal change of the left ventricle.

FIG. 9 is a display screen for measuring a temporal change of the left ventricle. In FIG. 9, a left ventricular volume change curve 221 is added to the display of FIG. 7.

The left ventricular volume change curve 221 is obtained by calculating the volume of a region, which is expressed by the points a to c, for each frame of the A2C image 202 with time as its horizontal axis and the volume as its vertical axis and making the graph.

As described above, in the second embodiment, the shape information of the target part of the object can be measured more accurately as in the first embodiment.

In addition, a unique effect of the second embodiment is that initial setting when measuring a temporal change is easy since it is necessary only to set the feature points first. In addition, the amount of operation may be a tracking operation of only feature points. Accordingly, since the operation time is shortened, the examination time can be shortened.

Third Embodiment

In a third embodiment of the present invention, an example will be described in which switching between contours extracted from the ventricle and the atrium or from the left ventricle and the right ventricle is performed.

In the third embodiment, the configuration of hardware of an ultrasonic diagnostic apparatus and S101 to S108 of software to execute are the same as those in the first embodiment. Accordingly, only the differences will be described.

Figure 10:
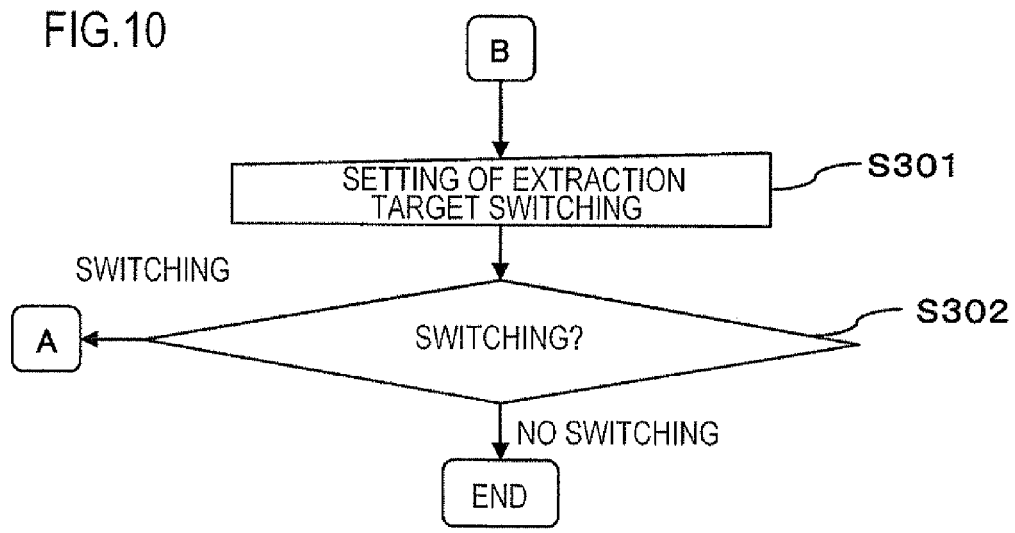
FIG. 10 is a flow chart showing the operation procedure of a third embodiment.

FIG. 10 is a flow chart showing the operation procedure of the third embodiment.

Since the third embodiment is performed subsequent to the determination of "appropriateness" in S108 of the first embodiment, the flow chart in FIG. 10 is connected to a terminal B of the flow chart in FIG. 2.

The examiner sets switching between contour extraction targets of the heart in an ultrasonic image, specifically, ventricle/atrium switching by the operation of the input unit 2. According to the operation of the input unit 2, the control unit 6 proceeds to S102 if there is "switching" from the ventricle to the atrium and ends the process if there is "no switching" from the ventricle to the atrium, for example (S301). Although the switching from the ventricle to the atrium is illustrated in S301, switching from the atrium to the ventricle or switching from the left ventricle to the right ventricle is also possible.

After switching to the atrium, connection to the terminal A of the flow chart in FIG. 2 is made and the control unit 6 executes S102 to S108 to display the contour of the atrium and measurement items on the output and display unit 1, and the process ends (S302).

In the third embodiment, a method of changing the feature point of an apical portion is shown. When changing the feature point of the apical portion is assumed, a feature point setting method shown in FIG. 11 may be considered.

Figure 11:
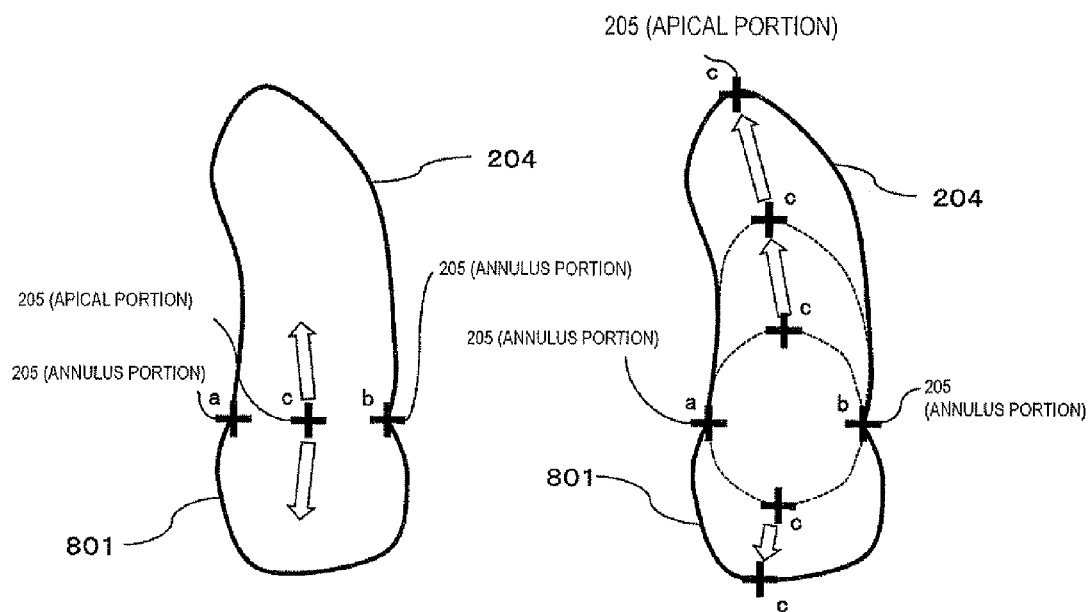
FIG. 11 is a view illustrating a feature point setting method for movement from the ventricle to the atrium in the third embodiment.

FIG. 11 is a view illustrating a feature point setting method for movement from the ventricle to the atrium in the third embodiment.

FIG. 11(*a*) is a view showing a case where an examiner sets the feature points a and b of an annulus portion and then sets the feature point c of the apical portion at the midpoint. Then, the control unit 6 extracts a contour while the examiner moves the position of the feature point c with an input device of the input unit 2.

When the examiner moves the feature point c in a direction approximately perpendicular to the line segment ab which connects the feature points a and b to each other (direction of white arrow in the drawing), the control unit 6 performs contour extraction whenever movement from the ventricle to the atrium is made as shown in FIG. 11(*b*) and displays the extracted contour on the output and display unit 1.

That is, the input unit 2 inputs the movement information of one of the feature points, and the contour position estimation unit 3 regenerates the initial contour by re-estimating the contour position of the target part by adjusting the center position, size, and inclination of the specified contour model data according to the movement information. In addition, the contour extraction unit 4 re-extracts a contour according to the movement information and the regenerated initial contour.

In the example of FIG. 11, the examiner can move the feature point c upward or downward from the line segment ab. For example, when the examiner moves the feature point c upward from the line segment ab, the left ventricle is selected as target tissue, and the control unit 6 executes S104 to S106. On the other hand, when the examiner moves the feature point c downward from the line segment ab, the left atrium is selected as target tissue, and the control unit 6 executes S104 to S106. As a result, a left atrium contour 801 can be extracted.

Figure 12:
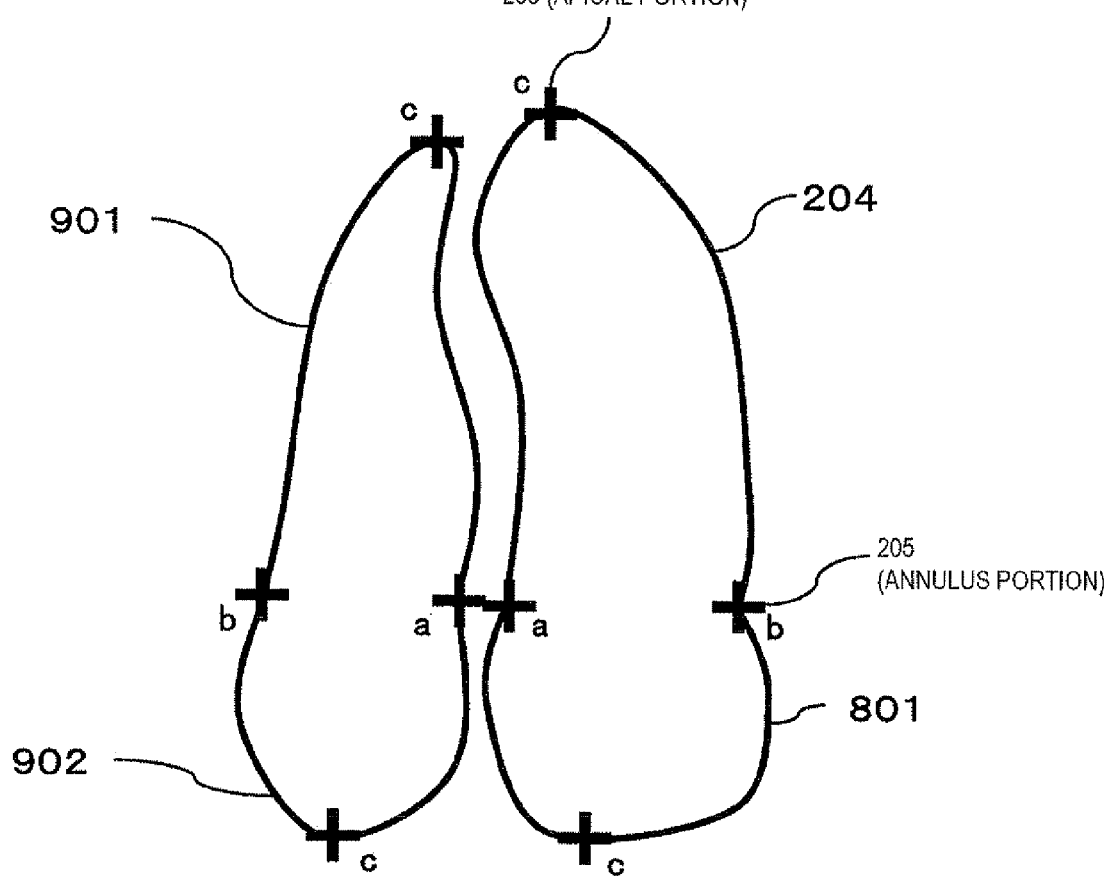
FIG. 12 is a view illustrating a feature point setting method for movement from the left ventricle to the right ventricle in the third embodiment.

In addition, in the example of FIG. 12, the left and right feature points a and b can be reversed so that movement from the left ventricle to the right ventricle is made.

FIG. 12 is a view illustrating a feature point setting method for movement from the left ventricle to the right ventricle in the third embodiment.

When the examiner exchanges the left and right feature points a and b with each other, the control unit 6 executes S104 to S106 for the right ventricle and the right atrium instantaneously so that a right ventricle contour 901 and a right atrium contour 902 can be extracted.

In addition, it is possible to set one contour line in one screen and change the feature points sequentially, or it is also possible to set a plurality of contour lines and measure a plurality of tissue parts simultaneously.

Figure 13:
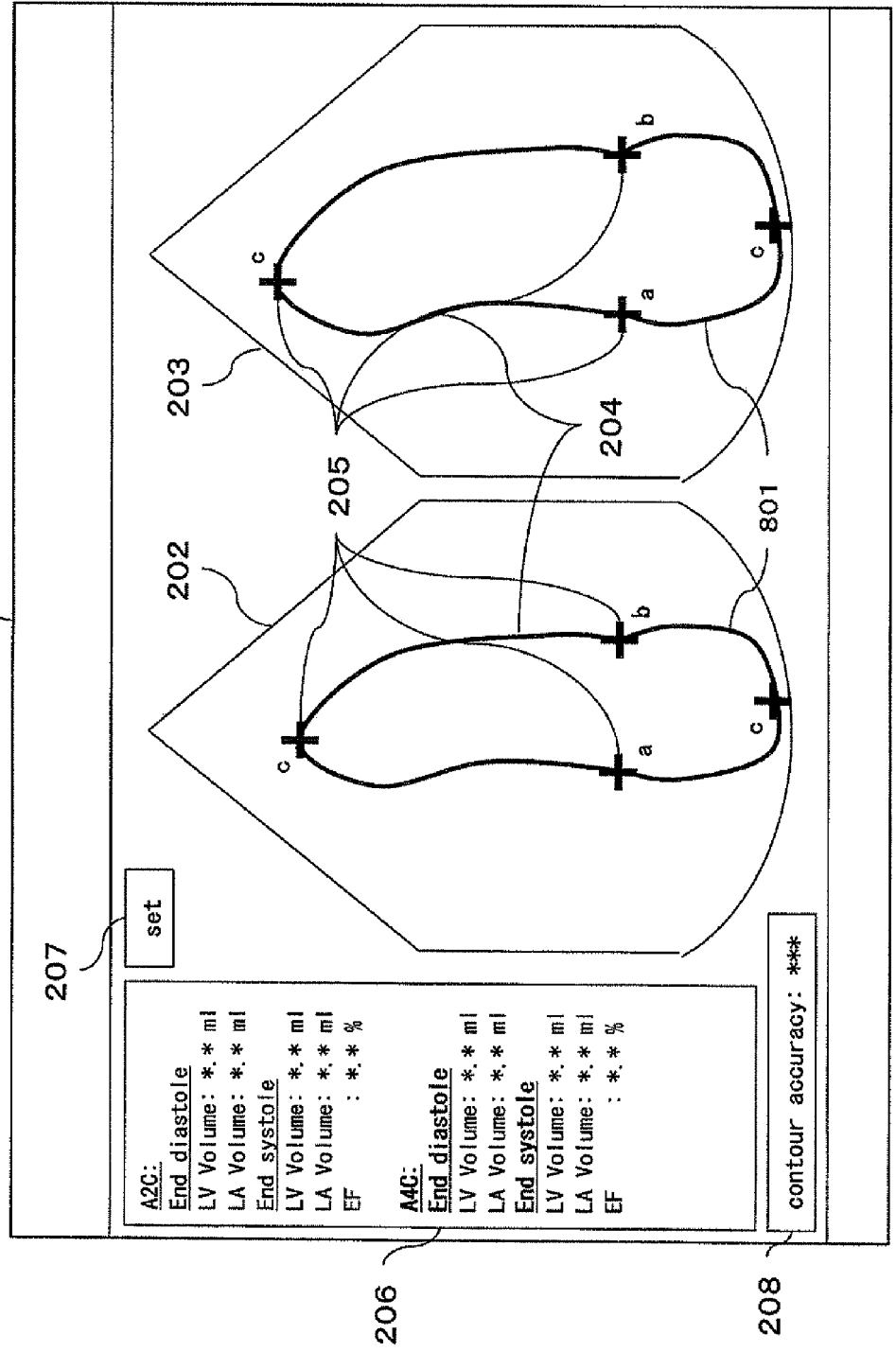
FIG. 13 is a view showing an example where the left ventricle and the left atrium are measured simultaneously and the measured values are displayed.

For example, a display screen shown in FIG. 13 may be considered. FIG. 13 is a view showing an example where the left ventricle and the left atrium are measured simultaneously and the measured values are displayed. Setting of feature points and contour extraction processing are performed separately from the left ventricle and the left atrium, and the contour line and the measured values are displayed in parallel. In addition, without being limited to the combination of the left ventricle and the left atrium, it is also possible to combine the right ventricle and the right atrium, measure a plurality of tissue parts, and display these results in parallel.

As described above, in the third embodiment, the shape information of the target part of the object can be measured more accurately as in the first embodiment.

In addition, a unique effect of the third embodiment is that a plurality of objects to be extracted can be observed simultaneously and accordingly it is possible to support the diagnostic imaging of a complex disease, which spans a plurality of target parts, for the examiner.

Fourth Embodiment

In a fourth embodiment of the present invention, an example will be described in which contour extraction is performed while changing the feature point or type of body tissue using an algorithm of a curve model instead of the contour model in the first embodiment.

In the fourth embodiment, the configuration of hardware of an ultrasonic diagnostic apparatus and S101 to S108 of software to execute are the same as those in the first embodiment. Accordingly, only the differences will be described.

In the fourth embodiment, a contour model (ACM, ASM, AAM, or the like) which changes its shape actively is used, and this is a useful algorithm when there is no high-speed operation processing function, such as a PC with many computation steps. When body tissue with a simple shape is a target, a curve model may be used as a simple model as in the fourth embodiment. Steps S104 and S105 differing from the first embodiment will mainly be described.

The control unit 6 generates an initial contour from the feature points 205 set in step S103 using the contour position estimation unit 3 (S104).

FIG. 14 is a view showing the contour extraction using the curve model of the fourth embodiment. The broken line of FIG. 14(a) is a curve which connects feature points, and is expressed by functions, such as a polynomial curve, a spline curve, and an elliptic curve. In addition, feature points d and e may be added as shown in FIG. 14(b), and a curve which connects the five feature points may be used. There is no limitation on the number of points.

The control unit 6 performs contour extraction processing using the contour extraction unit 4 (S105). As shown in FIG. 14(a), boundary detection processing on the left ventricle wall surface is performed with the curve as a reference in order to change the shape of the contour in the direction of the arrow, thereby obtaining the left ventricle contour 204.

When the contour extraction processing is not performed, a display of an initial contour (broken line) by a curve model 1001 in FIG. 14 is obtained when changing feature points. In this case, the feature points are moved to check a curve of a broken line, and the examiner performs manual fine adjustment using the input unit 2.

As described above, in the fourth embodiment, the shape information of the target part of the object can be measured more accurately as in the first embodiment.

In addition, a unique effect of the fourth embodiment is that the amount of processing operations when changing feature points is reduced by using the simple curve model even if the process is heavy and unstable when a contour model is used. As a result, a stress-free operation becomes possible.

Fifth Embodiment

In a fifth embodiment of the present invention, an example will be described in which the accuracy of a model is reduced to improve real time efficiency of an operation when changing the feature points or type of body tissue and a high-accuracy model is applied to increase the extraction accuracy of a contour when the feature points or the type is determined.

In the fifth embodiment, the configuration of hardware of an ultrasonic diagnostic apparatus and S101 to S108 of software to execute are the same as those in the third embodiment. Accordingly, only the differences will be described.

The control unit 6 extracts a contour from the initial contour generated in S104 using the contour extraction unit 4 (S105). In this case, the accuracy of the extracted contour is set low. In the case of contour models such as ACM, ASM, and AAM used in the third embodiment, processing for reducing the amount of computation, such as reducing the number of repetitions to converge the contour or reducing the number of control points, is performed. In the case of the curve model used in the fourth embodiment, processing for reducing the amount of computation, such as dropping the number of dimensions of the function expressing the curve, is performed.

Figure 15:
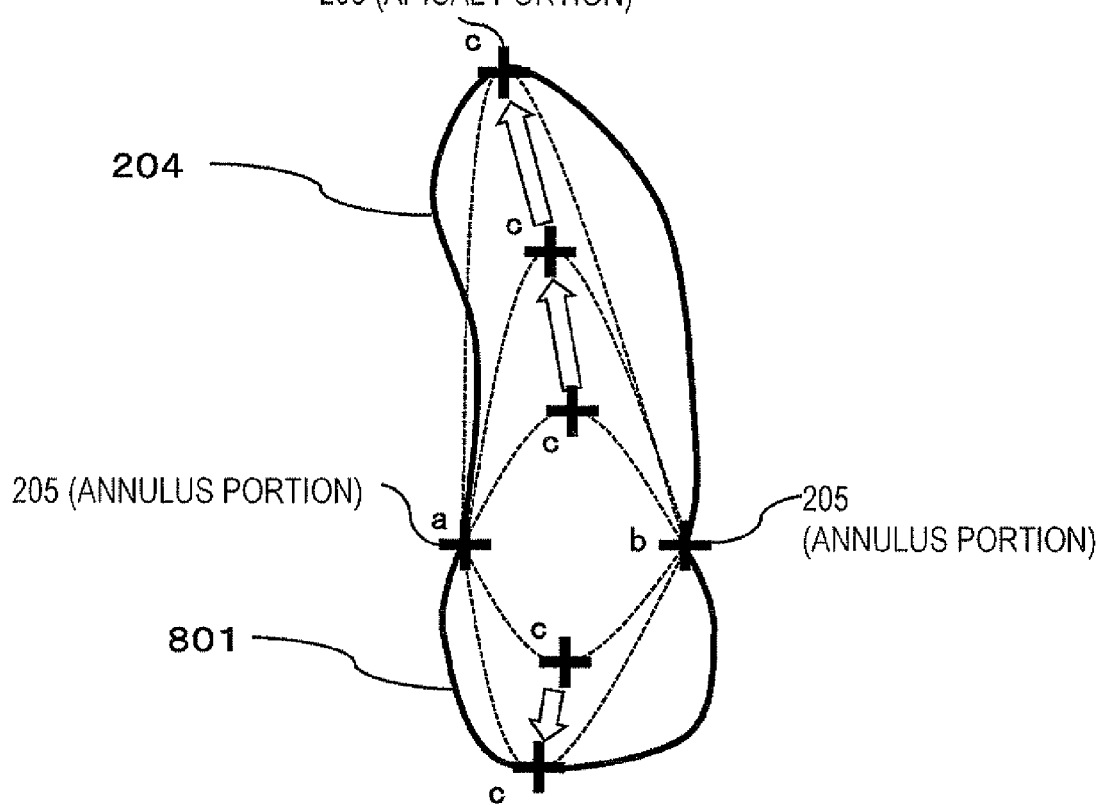
FIG. 15 is a view illustrating the contour extraction of a contour of a fifth embodiment.

FIG. 15 is a view illustrating the rough contour extraction in the fifth embodiment.

The broken line of FIG. 15 is the contour generated in S105, and is a rough contour compared with those shown in the first to fourth embodiments.

The control unit 6 changes the contour generated in S105 when necessary by the operation of the feature point change in S103.

That is, when the feature points are moved to change the positions, the initial contour is generated (S104). Then, contour extraction processing (S105) and measurement item calculation (S107) are performed, and the contour and the measured values of the measurement items are displayed. The examiner adjusts the contour shape by moving the feature points so as to become close to the actual contour while checking the contour and the measured values of the measurement items on a screen.

Then, the examiner checks and inputs the rough contour by operating the input device of the input unit 2.

By determination of the rough contour, the control unit 6 performs the generation of an initial contour (S104), contour extraction processing (S105), and calculation of measurement items (S107) using the rough contour as feature points. In this case, however, the accurate contour extraction processing described in the first to fourth embodiments is performed without reducing the amount of computation unlike the rough contour extraction.

As described above, in the fifth embodiment, the shape information of the target part of the object can be measured more accurately as in the first embodiment.

In addition, a unique effect of the fifth embodiment is that the positions, at which normal feature points are set, are nearby since a rough contour is displayed before the places where feature points for performing normal contour extraction are located are set, and accordingly, it is possible to shorten the movement distance for manual correction of the position of the contour in particular.

Sixth Embodiment

In a sixth embodiment of the present invention, an example will be described in which there is a desired contour point to be moved and the shape of only the contour line placed around the contour point is restrictively changed.

In the sixth embodiment, the configuration of hardware of an ultrasonic diagnostic apparatus and S101 to S108 of software to execute are the same as those in the first embodiment. Accordingly, only the differences will be described.

FIG. 16 is a view showing an example of the sixth embodiment where the number of feature points is not 3 but 4.

The control unit 6 sets a feature point d in S103, and the examiner adjusts a contour line around only the feature point d. The feature point d is a point designated on the contour line by the input unit 2. In addition, the positions of the feature points a to d can be moved by the examiner. For the operation in this case, a case where the feature point d is moved will be described.

When the feature point d is moved, the examiner changes the shape of only the contour line between the feature points c and b adjacent to the feature point d as shown in FIG. 16(b) (modification of S105). The control unit 6 may perform contour shape change processing on only (broken line) between the feature points c and b, or may perform contour shape change processing on all contour points and then replace only (solid line) between the feature points a and c with the contour line before the contour shape change. In addition, it is assumed that the examiner can select freely a range from the feature point d to an adjacent point, the shape of which is to be changed, using the input device.

As described above, in the sixth embodiment, the shape information of the target part of the object can be measured more accurately as in the first embodiment.

In addition, a unique effect of the sixth embodiment is that fine adjustment of a part of the contour line is possible since the shape of only a part of the contour line can be changed and accordingly, it is possible to extract a contour which fits the shape of the heart chamber more.

Seventh Embodiment

A seventh embodiment is a method of estimating the number and shapes of contour lines to be extracted from the measurement items or the plurality of feature points indicating body tissue, which have been set by the examiner, and determining the position of the more detailed contour.

Figure 17:
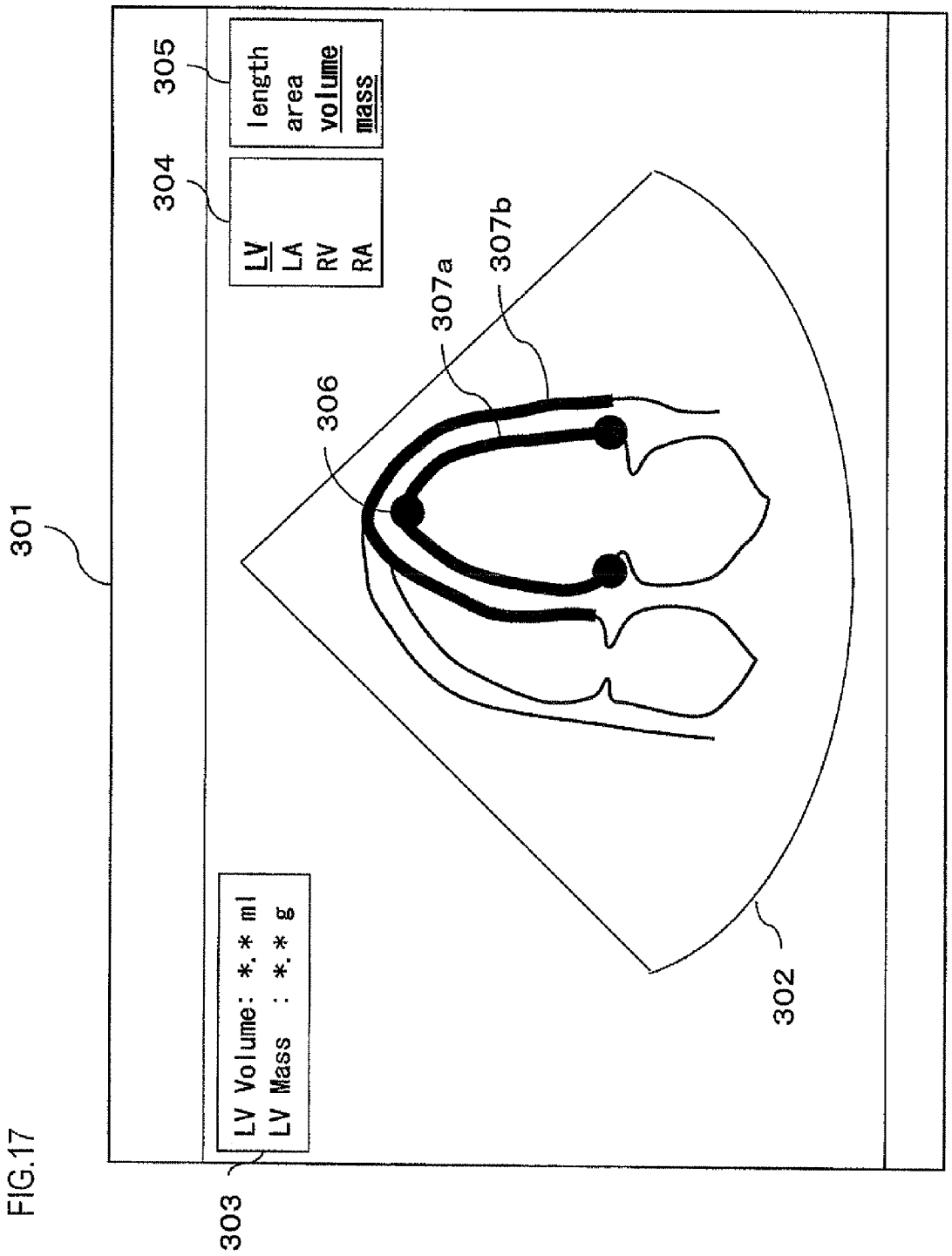
FIG. 17 is a first example of the screen on which an ultrasonic image, contours, and a measurement result are displayed in a seventh embodiment.
Figure 18:
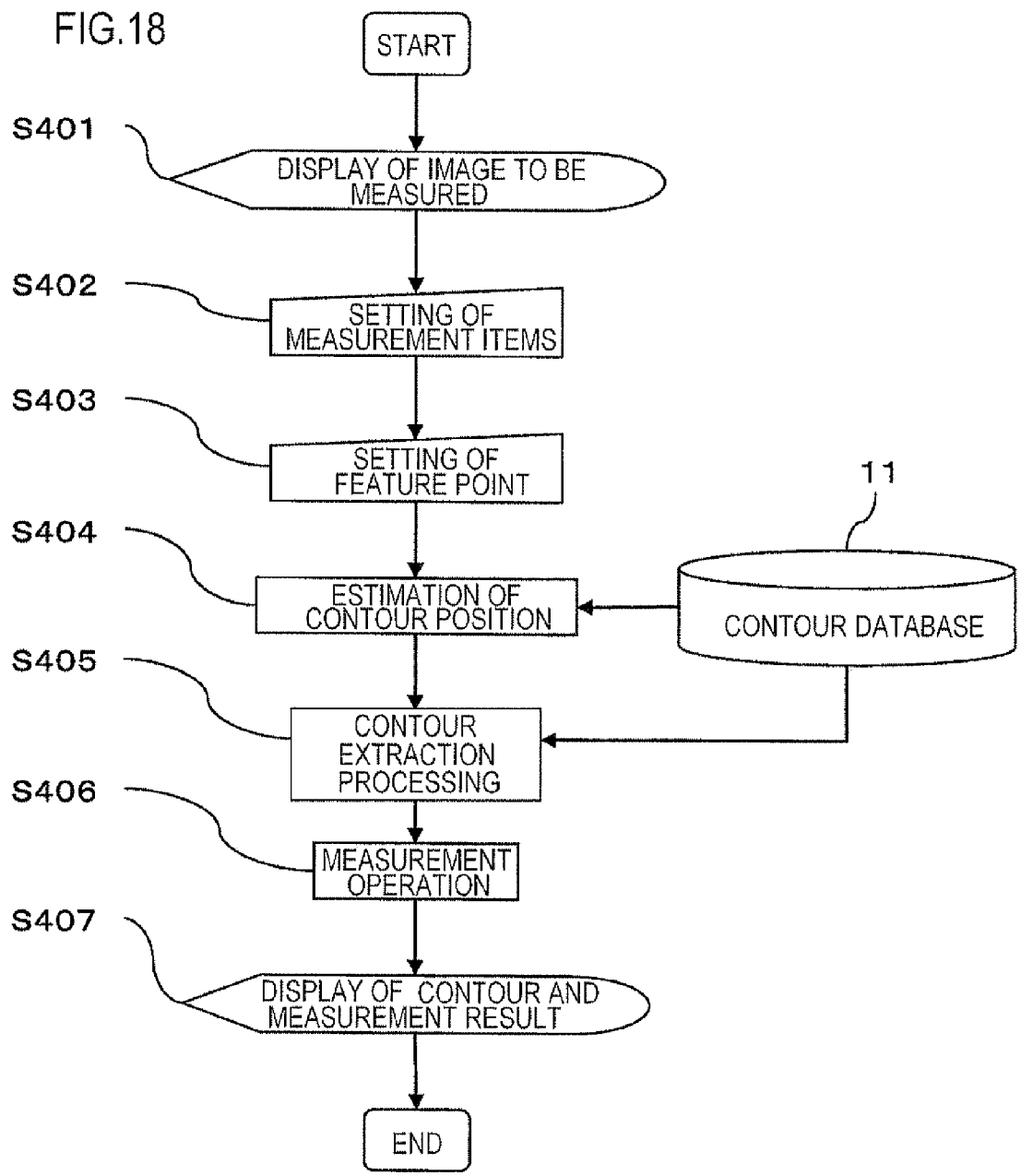
FIG. 18 is a flow chart of the seventh embodiment.

Explanation will be given according to the flow of processing shown in the flow chart of FIG. 18. First, the control unit 6 displays an image, in which target body tissue has been extracted, on the display screen of the output and display unit 1 (S401). Here, an example will be described in which an apical four chamber image 302 is displayed for measurement of the left ventricle, like a display screen 301 in FIG. 17.

Then, for the body tissue displayed on the screen, the examiner sets the type of body tissue to be measured using the input unit 2 (S402). A type 304 of body tissue to be measured is displayed on the upper right of FIG. 17. If it is the heart, items of LV (left ventricle), LA (left atrium), RV (right ventricle), and RA (right atrium) are displayed. The examiner selects body tissue to be measured from these. Here, an example is shown in which the LV is selected (shown with bold and underlined letters in FIG. 17).

Then, the examiner sets a measurement item for the body tissue, which is displayed on the screen, using the input unit 2 (S402). A measurement item 305 is displayed on the upper right of FIG. 17, and the examiner selects one or more from length (contour length), area, volume, and mass (myocardial weight). In addition to those shown in FIG. 17, other necessary items may be set as the measurement item 305. Here, an example is shown in which volume and mass are selected (shown with bold and underlined letters in FIG. 17).

Then, the examiner sets a feature point 306 for the body tissue, which is displayed on the screen, using the input unit 2 (S403). Here, an example will be described in which two points of an annulus portion of the left ventricle and one point of an apical portion of the left ventricle are designated in order to show the position of the left ventricle. In addition, the two points of the annulus portion of the left ventricle may be set automatically, and the examiner may designate only one point of the apical portion of the left ventricle.

Then, the contour position estimation unit 3 of the apparatus estimates the contour position (S404). Here, it can be seen by the input information in S402 that the volume of the LV and the myocardial weight need to be measured. Therefore, two contours are needed, and it is necessary to perform extraction at the positions of the intima and the adventitia of the left ventricle (refer to first and second contours 307a and 307b in FIG. 17). In the related art, it is necessary to set the feature point for each contour. In the present embodiment, however, when a plurality of contours of a target part are present, the contour position estimation unit 3 generates a first initial contour by estimating a first contour position using the feature points set in S403 and also generates a second initial contour by estimating a second contour position using the first initial contour. Therefore, measurement items and the number of necessary contours are associated with each other in advance, and the position of the feature point and the position of the contour are stored in a contour database 11 so as to be associated with each other. For example, the type of body tissue and measurement items and an estimation model for estimating the contour position are stored in the contour database 11 so as to match each other. Moreover, for example, the type of body tissue and measurement items and an estimation program for estimating the contour position are stored in the storage unit 9 so as to match each other.

Figure 19:
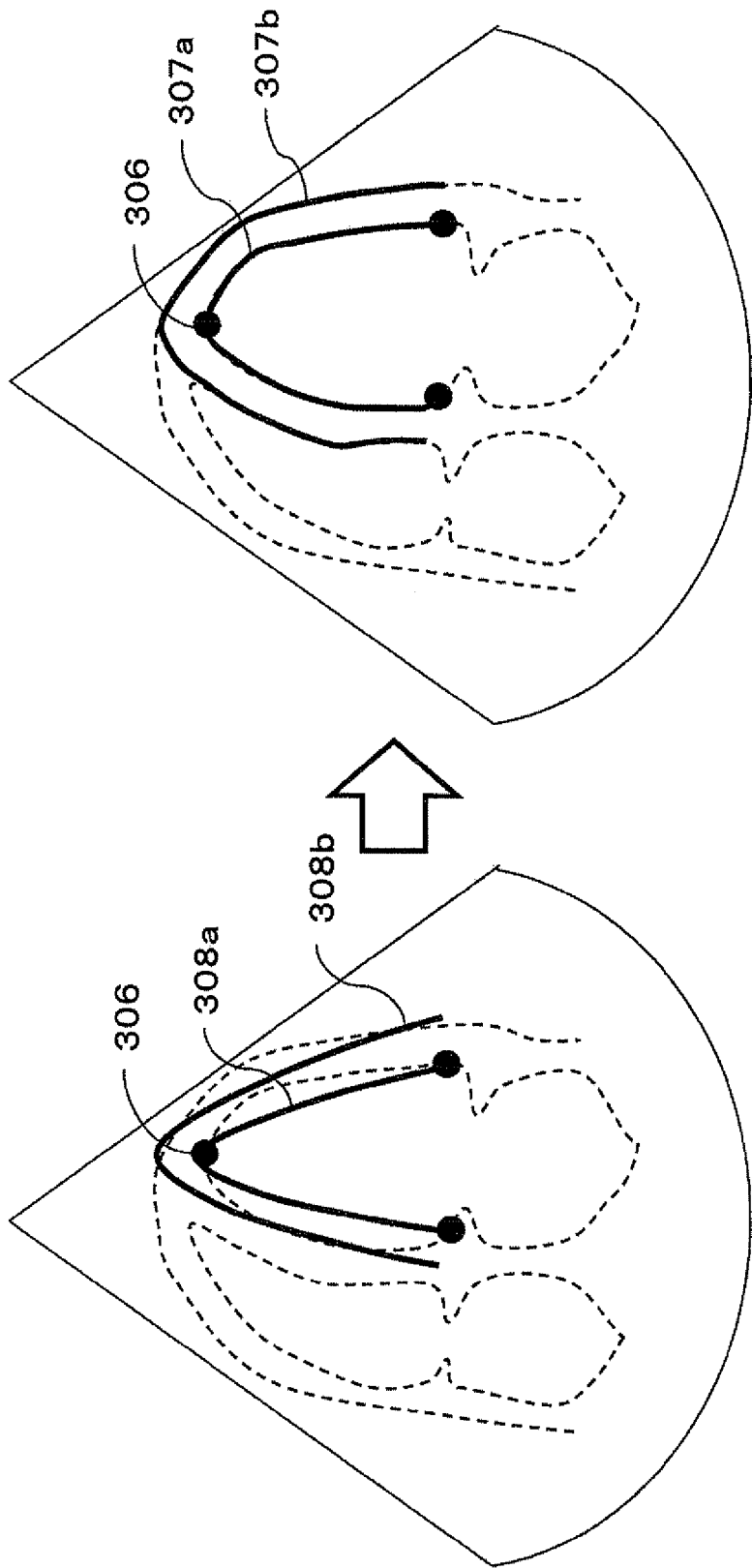
FIG. 19 is a view illustrating the contour position estimation and the contour extraction processing of the seventh embodiment.

As described above, estimation models for extracting the contours required for measuring various measurement items or feature points, for example, are stored in the contour database 11. The estimation models are contours set by other images in the past or contour models generalized by statistical analysis of them. Here, the contour position estimation unit 3 specifies an estimation model for extracting contours of the intima and the adventitia of the left ventricle when two points of the annulus portion and one point of the apical portion are designated. The left drawing of FIG. 19 is an example of a screen on which first and second initial contours 308a and 308b are displayed so as to overlap an ultrasonic image. However, they may not be displayed in practice. For example, this estimation model includes first contour model data, which passes through two points of the annulus portion and one point of the apical portion, at the intima side and second contour model data, which is equivalent to the adventitia, at positions at the adventitia side which are located at fixed distances from the intima side. Here, various curves may be set as the contour model data, and the contour model data may be defined on the basis of the contour measured in the past.

The contour position estimation unit 3 generates the first initial contour 308a by estimating a first contour position by adjusting the center position, size, and inclination of the first contour model data included in the estimation model according to the positions of the set feature points. In addition, the contour position estimation unit 3 generates the second initial contour 308b by estimating a second contour position using the generated first initial contour 308a. For example, the contour position estimation unit 3 generates the second initial contour 308b by estimating the second contour position by adjusting the center position, size, and inclination of the second contour model data included in the estimation model such that each point of the first initial contour 308a and each corresponding point of the second initial contour 308b are separated from each other by a fixed distance in a predetermined direction (in the present embodiment, the second initial contour 308b is located in a direction of the outside of the first initial contour 308a).

As another method, an estimation program stored in the storage unit 9 may be used without using the contour database 11. A method of calculating a contour mathematically, which is matched with the set measurement item or the set position of body tissue, is stored in advance in the estimation program. According to this program, the contour position is estimated to generate the initial contour. For example, if a contour can be expressed as a polynomial function, coefficients of the polynomial function can be determined from the position or the size of tissue.

The contour position estimation unit 3 generates the first initial contour 308a by estimating a first contour position by adjusting the center position, size, and inclination of the first contour model data, which are calculated by the estimation program, according to the positions of the set feature points. In addition, the contour position estimation unit 3 generates the second initial contour 308b by estimating a second contour position using the generated first initial contour 308a. For example, the contour position estimation unit 3 generates the second initial contour 308b by estimating the second contour position by adjusting the center position, size, and inclination of the second contour model data calculated by the estimation program such that each point of the first initial contour 308a and each corresponding point of the second initial contour 308b are separated from each other by a fixed distance in a predetermined direction (in the present embodiment, the second initial contour 308b is located in a direction of the outside of the first initial contour 308a).

Then, the contour extraction unit 4 of the apparatus extracts a contour in detail (S405). Since a rough position of the contour is determined by the contour position estimation of S404, the position of the contour is determined in more detail here. Processing starts from the contour in the left drawing of FIG. 19 to fit the intima and the adventitia of the left ventricle shown in the right drawing of FIG. 19.

Specifically, the contour extraction unit 4 performs boundary detection processing for a predetermined range in a direction, which crosses contour points and is perpendicular to the first initial contour 308a, for each contour point on the first initial contour 308a. The boundary detection processing is as described in the first embodiment. In addition, the contour extraction unit 4 moves the contour point to the position detected as the "boundary". However, as an exception, the feature point of the first initial contour 308a is controlled so as to pass through the set position, without performing the boundary detection processing.

That is, the contour extraction unit 4 extracts a contour so as to pass through the feature points and the contour point after being moved to the position detected as the "boundary".

In this way, the first contour (intima contour of the left ventricle) 307a can be extracted.

Then, the contour extraction unit 4 performs boundary detection processing for a predetermined range, which crosses contour points in a direction perpendicular to the second initial contour 308b, for each contour point on the second initial contour 308b. The boundary detection processing is as described in the first embodiment. In addition, the contour extraction unit 4 moves the contour point to the position detected as the "boundary".

That is, the contour extraction unit 4 extracts a contour so as to pass through the contour point after being moved to the position detected as the "boundary".

In this way, the second contour (adventitia contour of the left ventricle) 307b can be extracted.

Then, the measurement unit 5 of the apparatus performs measurement of measurement items using the coordinate information of the extracted contour (S406). Here, since the volume of the left ventricle and the myocardial weight of the left ventricle are calculated, the Area-length method or the Modified Simpson method can be applied in the former case and the Area-length method or the Truncated ellipsoid method can be applied in the latter case, for example. In addition, it is also possible to calculate the volume of the myocardium by subtracting the volume of a portion surrounded by the intima from the volume of a portion surrounded by the adventitia and to calculate the myocardial weight by multiplying this by the specific gravity.

Then, the output and display unit 1 of the apparatus outputs the ultrasonic image 302, the first contour 307a, the second contour 307b, and a measured value 303 (S407). As shown in FIG. 17, the first and second contours 307a and 307b are displayed so as to overlap the ultrasonic image 302. As the measured value 303, the item and the numeric value are displayed on a screen.

Figure 20:
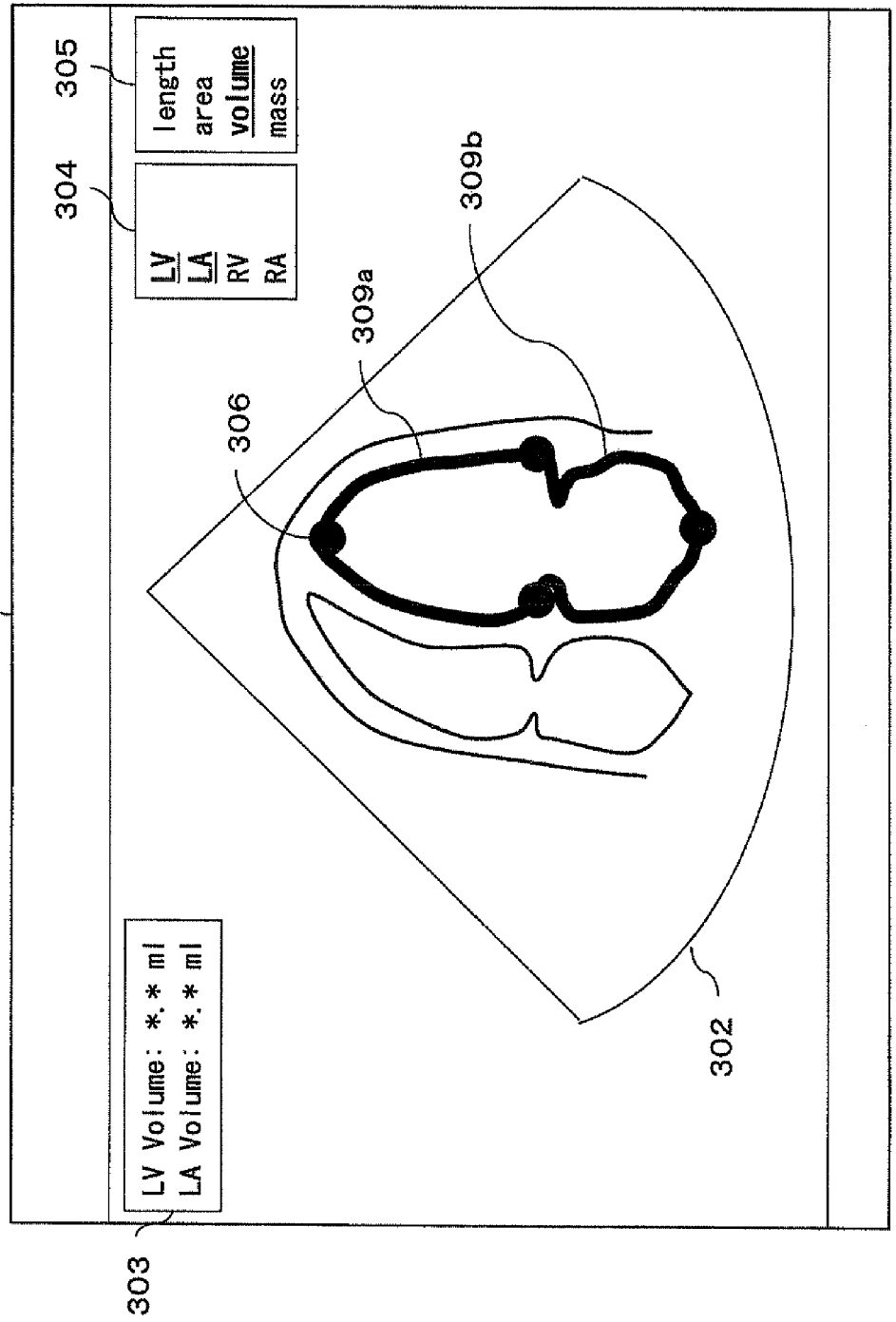
FIG. 20 is a second example of the screen on which an ultrasonic image, contours, and a measurement result are displayed in the seventh embodiment.

Other contour extraction examples are shown referring to FIG. 20.

The examiner sets a measurement item for body tissue, which is displayed on the screen, using the input unit 2 (S402). In FIG. 20, parts to be measured are LV and LA, and only the volume is a measurement item.

Then, the examiner sets a feature point 306 for the body tissue, which is displayed on the screen, using the input unit 2 (S403). Here, the feature points 306 are set as two points of the annulus portion, one point of the apical portion, and one point of a lower portion of the left atrium.

For example, the contour position estimation unit 3 of the apparatus generates a first initial contour by estimating a first contour position by reading the first contour model data matched with the left ventricle from the contour database 11 and adjusting the center position, size, and inclination of the contour model data on the basis of the feature points 306 (two points of the annulus portion and one point of the apical portion). In addition, the contour position estimation unit 3 of the apparatus generates a second initial contour by estimating a second contour position by reading the second contour model data matched with the left atrium from the contour database 11 and adjusting the center position, size, and inclination of the second contour model data on the basis of the first initial contour and the feature point 306 (one point of a lower portion of the left atrium) (S404).

Then, the contour extraction unit 4 of the apparatus performs contour extraction processing in detail to extract first and second contours 309a and 309b as shown in FIG. 20 (S405).

As described above, according to the seventh embodiment, when a plurality of contours of a target part are present, the contour position estimation unit 3 generates the first initial contour by estimating the first contour position using the feature points and also generates the second initial contour by estimating the second contour position using the first initial contour. Specifically, the apparatus stores the type of body tissue and measurement items and an estimation model or an estimation program for estimating the contour position in the storage unit 9 so as to match each other. The input unit 2 inputs the type of body tissue and measurement items, and the contour position estimation unit 3 generates the first initial contour by estimating the first contour position by specifying the estimation model or the estimation program on the basis of the type of body tissue and the measurement items input by the input unit 2 and executing processing according to the specified estimation model or estimation program. In addition, the contour position estimation unit 3 generates the second initial contour by estimating the second contour position by executing processing according to the specified estimation model or estimation program on the basis of the first initial contour.

According to the seventh embodiment, when a target to be measured needs a plurality of contours, the examiner can extract a plurality of contours related to the measurement part by setting the type of body tissue to be measured and measurement items first and designating the feature points related to one contour. Therefore, time and effort of the examiner to set the feature points are reduced. This can contribute to shortening of the examination time.

As described above, in the constituent components of the medical image diagnostic apparatus or the medical image contour extraction processing method of the present invention, the output and display unit 1 displays a medical image including a target part of an object, the input unit 2 inputs feature points of the target part, the initial contour generation unit 3 generates the initial contour by estimating a contour position of the target part, the contour extraction unit 4 extracts a contour along the shape of the target part using the feature points and the initial contour, and the control unit 6 displays a composite image obtained by combining the extracted contour and the medical image on the output and display unit 1. Therefore, since a contour along the shape of the target part using the initial contour and the feature points is extracted, a contour along the shape of a moving organ can be extracted every contour extraction operation when the target part is a moving organ with large individual difference of an object. As a result, the accuracy in extracting the target part of the object can be improved.

While the measurement of the heart in the ultrasonic diagnostic apparatus has been described above as an example, the present invention may be similarly applied to other diagnostic apparatuses and body tissue.

REFERENCE SIGNS LIST

1: output and display unit
2: input unit
3: initial contour generation unit
4: contour extraction unit
5: measurement unit
6: control unit

The invention claimed is:

1. A medical image diagnostic apparatus comprising:
an image display that displays a medical image including a target part of an object;
an input device that enables a user to input a type and feature points of the target part; and
a processor, the processor comprising a control unit, the control unit configured to control:
a contour model specifying unit for specifying a contour model, which is stored in a first storage unit, based on the type of the target part;
a contour position estimator that estimates a contour position of the target part to generate an initial contour by adjusting a shape information of a contour model data, which is specified by the contour model specifying unit, in accordance with positions of the feature points; and
a contour extractor that extracts a contour along a shape of the target part by fitting the initial contour to a contour of the target part with moving an edge of the initial contour to a wall surface of the contour of the target part, along with moving feature points of the initial contour towards a location of the feature points of the target part;
wherein a shape of the initial contour is expressed by a first group of positions placed on a curve line and a second group of positions corresponding to the feature points of the initial contour, and when the contour extractor extracts the contour, the shape of the initial contour changes by moving the first group of positions closer to the wall surface of myocardium, using a boundary detection processing, and by moving the second group of positions in a direction towards the feature points of the target part, such that the extracted contour passes through the feature points of the target part, wherein the feature points of the initial contour are different than the feature points of the target part; and
wherein the control unit is further configured to display a composite image that is obtained by combining the extracted contour and the medical image, on the image display.

2. The medical image diagnostic apparatus according to claim 1, wherein:
the first storage unit stores the contour model data for each type of body tissue related to the target part,
wherein the input device inputs the type of the body tissue, and
the contour position estimator generates the initial contour by estimating a contour position of the target part by specifying the contour model data on the basis of the input type of the body tissue and adjusting the center position, size, and inclination of the specified contour model data according to positions of the feature points of the target part.

3. The medical image diagnostic apparatus according to claim 2, wherein the control unit is further configured to control:
 a measurement unit that calculates measurement items regarding the length, area, and volume of a contour-extracted region from the contour extracted by the contour extractor.

4. The medical image diagnostic apparatus according to claim 3, further comprising:
 a second storage unit that stores the type of the body tissue and the measurement items and an estimation model or an estimation program for estimating the contour position so as to match each other,
 wherein the input device inputs the type of the body tissue and the measurement items, and
 the contour position estimator generates the initial contour by estimating the contour position by specifying the estimation model or the estimation program on the basis of the type of the body tissue and the measurement items input by the input device and executing processing according to the specified estimation model or estimation program.

5. The medical image diagnostic apparatus according to claim 2,
 wherein, when a plurality of contours of the target part are present, the contour position estimator generates a first initial contour by estimating a first contour position using the feature points of the target part and also generates a second initial contour by estimating a second contour position using the first initial contour.

6. The medical image diagnostic apparatus according to claim 5, wherein the input device inputs the type of the body tissue, and
 the contour position estimator generates the first initial contour by estimating a contour position of the target part by specifying the contour model data on the basis of the input type of the body tissue and adjusting the center position, size, and inclination of the specified contour model data according to positions of the feature points of the target part.

7. The medical image diagnostic apparatus according to claim 5,
 wherein the contour extractor performs the boundary detection processing for a predetermined range in a direction, which crosses a contour point and is perpendicular to the first initial contour, for each contour point on the initial contour and moves the contour point to a position detected as a boundary by the boundary detection processing and also extracts a contour so as to pass through the feature points of the target part and the contour point after the movement.

8. The medical image diagnostic apparatus according to claim 5,
 wherein the input device inputs movement information of at least one of the feature points of the target part,
 the contour position estimator regenerates the first initial contour by re-estimating the contour position of the target part by adjusting the center position, size, and inclination of the specified contour model data according to the movement information, and
 the contour extractor re-extracts a contour according to the movement information and the regenerated first initial contour.

9. The medical image diagnostic apparatus according to claim 5, further comprising:
 a measurement unit that calculates measurement items regarding the length, area, volume, and the like of a contour-extracted region from the contour extracted by the contour extractor.

10. The medical image diagnostic apparatus according to claim 9, further comprising:
 a second storage unit that stores the type of the body tissue and the measurement items and an estimation model or an estimation program for estimating the contour position so as to match each other,
 wherein the input device inputs the type of the body tissue and the measurement items, and
 the contour position estimator generates the initial contour by estimating the contour position by specifying the estimation model or the estimation program on the basis of the type of the body tissue and the measurement items input by the input device and executing processing according to the specified estimation model or estimation program.

11. The medical image diagnostic apparatus according to claim 5, further comprising:
 a switching setting unit that performs switching setting of a plurality of extracted regions of the target part.

12. The medical image diagnostic apparatus according to claim 1,
 wherein the contour extractor performs the boundary detection processing for a predetermined range in a direction which crosses a contour point and is perpendicular to the initial contour, for each contour point on the initial contour, and moves the contour point to a position detected as a boundary by the boundary detection processing and also extracts a contour so as to pass through the feature points of the target part and the contour point after the movement.

13. The medical image diagnostic apparatus according to claim 1,
 wherein the input device inputs movement information of at least one of the feature points of the target part,
 the contour position estimator regenerates the initial contour by re-estimating the contour position of the target part by adjusting the center position, size, and inclination of the specified contour model data according to the movement information, and
 the contour extractor re-extracts a contour according to the movement information and the regenerated initial contour.

14. The medical image diagnostic apparatus according to claim 1, wherein the control unit is further configured to control:
 a switching setting unit that performs switching setting of a plurality of extracted regions of the target part.

15. A medical image contour extraction processing method comprising:
 a step of displaying a medical image including a target part of an object by means of an image display;
 a step of inputting feature points of the target part by means of an input device;
 a step of estimating a contour position of the target part to generate an initial contour by means of a contour position estimator;
 a step of extracting a contour along a shape of the target part using the feature points and the initial contour by means of a contour extractor, the extracting being based upon a fitting of an initial contour to a contour of a target part with moving an edge of the initial contour to a wall surface of the contour of the target part, along with moving feature points of the initial contour towards a location of the feature points of the target part; and a step of displaying a composite image, which is obtained by combining the extracted contour and the medical image, on the image display by means of a controller, wherein a shape of the initial contour is expressed by a first group of positions placed on a curve line and a second group of positions corresponding to the feature points of the initial contour, and during the extracting the contour, the shape of the initial contour changes by moving the first group of positions closer to the wall surface of myocardium, using a boundary detection processing, and by moving the second group of positions in a direction towards the feature points of the target part, such that the extracted contour passes through the feature points of target part, and wherein the feature points of the initial contour are different than the feature points of the target part.

* * * * *